(12) United States Patent
Alli et al.

(10) Patent No.: US 9,125,808 B2
(45) Date of Patent: *Sep. 8, 2015

(54) IONIC SILICONE HYDROGELS

(71) Applicant: Johnson & Johnson Vision Care, Inc., Jacksonville, FL (US)

(72) Inventors: Azaam Alli, Jacksonville, FL (US); James D. Ford, Orange Park, FL (US); Douglas G. Vanderlaan, Jacksonville, FL (US); Scott L. Joslin, Ponte Vedra Beach, FL (US); Shivkumar Mahadevan, Orange Park, FL (US); Thomas L. Maggio, Jacksonville, FL (US); Ranganath Raja, Jacksonville, FL (US); Sharmila Muthukrishnan, Chennai (IN); C. Surendran, The Nilgris (IN); R. Sridharan, Chennai (IN)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 98 days.

This patent is subject to a terminal disclaimer.

(21) Appl. No.: 13/829,688

(22) Filed: Mar. 14, 2013

(65) Prior Publication Data

US 2013/0217620 A1 Aug. 22, 2013

Related U.S. Application Data

(63) Continuation-in-part of application No. 13/720,286, filed on Dec. 19, 2012.

(60) Provisional application No. 61/579,683, filed on Dec. 23, 2011.

(51) Int. Cl.
*C08F 290/06* (2006.01)
*G02B 1/04* (2006.01)
*A61K 8/72* (2006.01)
*C08G 61/02* (2006.01)
*G02C 7/00* (2006.01)
*G02C 7/02* (2006.01)
*G02C 5/00* (2006.01)
*A61K 9/00* (2006.01)
*C08G 77/16* (2006.01)

(52) U.S. Cl.
CPC .............. *A61K 9/0051* (2013.01); *G02B 1/043* (2013.01); *C08G 77/16* (2013.01)

(58) Field of Classification Search
CPC ...... A61K 9/0051; G02B 1/043; C08G 77/16; C08L 101/14; C08L 83/104; C08L 51/085
USPC ................ 523/107, 106, 105, 1; 351/159.02, 351/159.01, 41
See application file for complete search history.

(56) References Cited

U.S. PATENT DOCUMENTS

| | | |
|---|---|---|
| 3,408,429 A | 10/1968 | Wichterle |
| 3,660,545 A | 5/1972 | Wichterle |
| 4,113,224 A | 9/1978 | Clark |
| 4,136,250 A | 1/1979 | Mueller |
| 4,139,513 A | 2/1979 | Tanaka |
| 4,153,641 A | 5/1979 | Deichert |
| 4,197,266 A | 4/1980 | Clark |
| 4,246,389 A | 1/1981 | LeBoeuf |
| 4,260,725 A | 4/1981 | Keogh |
| 4,495,313 A | 1/1985 | Larsen |
| 4,810,764 A | 3/1989 | Friends |
| 4,837,289 A | 6/1989 | Mueller et al. |
| 5,314,961 A | 5/1994 | Anton et al. |
| 5,358,995 A | 10/1994 | Lai et al. |
| 5,387,662 A | 2/1995 | Kunzler et al. |
| 5,486,579 A | 1/1996 | Lai et al. |
| 5,712,327 A | 1/1998 | Chang et al. |
| 5,998,498 A | 12/1999 | Vanderlaan et al. |
| 6,020,445 A * | 2/2000 | Vanderlaan et al. .......... 526/279 |
| 6,367,929 B1 | 4/2002 | Maiden et al. |
| 6,602,930 B2 | 8/2003 | Imafuku |
| 6,762,264 B2 | 7/2004 | Kunzler et al. |
| 6,867,245 B2 | 3/2005 | Iwata |
| 6,902,812 B2 | 6/2005 | Valint, Jr. |
| 6,943,203 B2 | 9/2005 | Vanderlaan et al. |
| 7,722,808 B2 | 5/2010 | Matsuzawa et al. |
| 7,934,830 B2 * | 5/2011 | Blackwell et al. ....... 351/159.33 |
| 8,367,746 B2 | 2/2013 | Manesis et al. |
| 2001/0044482 A1 * | 11/2001 | Hu et al. ..................... 523/106 |

(Continued)

FOREIGN PATENT DOCUMENTS

| | | |
|---|---|---|
| WO | 0170837 A1 | 9/2001 |
| WO | 03022321 A2 | 3/2003 |

(Continued)

OTHER PUBLICATIONS

"The role of ionic hydrophilic monomers in silicone hydrogels for contact lens application", Lai, Y., Valint, P., and Friends, G.; 213th ACS National Meeting, San Francisco, Apr. 13-17, 1997.

(Continued)

*Primary Examiner* — Ling Choi
*Assistant Examiner* — Jessica E Whiteley
(74) *Attorney, Agent, or Firm* — Karen A. Harding

(57) ABSTRACT

The present invention relates to ionic silicone hydrogel contact lenses which comprise at least one pharmaceutical or nutriceutical component and are formed from reaction mixtures comprising a mixture of slow-reacting hydrophilic monomers, including at least one slow-reacting ionic monomer, at least one silicone-containing component and at least one hydroxyl-containing component, wherein the ratio of the slow-reacting hydrophilic component half lives to the silicone-containing component half life is at least 2.

92 Claims, 3 Drawing Sheets

(56) References Cited

U.S. PATENT DOCUMENTS

| | | |
|---|---|---|
| 2002/0016383 A1 | 2/2002 | Iwata et al. |
| 2002/0107324 A1 | 8/2002 | Vanderlaan |
| 2004/0039077 A1 | 2/2004 | Baba et al. |
| 2006/0063852 A1 | 3/2006 | Iwata et al. |
| 2006/0187410 A1 | 8/2006 | Sato et al. |
| 2006/0229423 A1 | 10/2006 | Parakka et al. |
| 2007/0066706 A1 | 3/2007 | Manesis et al. |
| 2007/0138692 A1 | 6/2007 | Ford et al. |
| 2008/0234457 A1* | 9/2008 | Zhou et al. ............... 528/25 |
| 2009/0060981 A1 | 3/2009 | Chauhan |
| 2010/0014047 A1* | 1/2010 | Chang et al. ............ 351/160 H |
| 2010/0048847 A1* | 2/2010 | Broad ........................ 526/263 |
| 2010/0249356 A1 | 9/2010 | Rathore |
| 2010/0280146 A1 | 11/2010 | Vanderlaan |
| 2011/0046332 A1 | 2/2011 | Breiner et al. |
| 2011/0230589 A1 | 9/2011 | Maggio |
| 2011/0237766 A1 | 9/2011 | Maggio |
| 2011/0275734 A1* | 11/2011 | Scales et al. ............... 523/107 |
| 2012/0214899 A1 | 8/2012 | Lee et al. |
| 2012/0216488 A1 | 8/2012 | Liu et al. |
| 2012/0216489 A1 | 8/2012 | Lee et al. |
| 2012/0218509 A1 | 8/2012 | Back et al. |
| 2012/0219387 A1 | 8/2012 | Atkinson et al. |
| 2012/0220688 A1 | 8/2012 | Wang et al. |
| 2012/0220689 A1 | 8/2012 | Yao et al. |
| 2012/0220743 A1 | 8/2012 | Francis et al. |
| 2012/0220744 A1 | 8/2012 | Liu et al. |
| 2013/0217620 A1 | 8/2013 | Alli et al. |
| 2014/0031447 A1* | 1/2014 | Alli et al. ............... 522/167 |

FOREIGN PATENT DOCUMENTS

| | | |
|---|---|---|
| WO | 03022322 A2 | 3/2003 |
| WO | 2004081105 A2 | 9/2004 |
| WO | 2008054667 A1 | 5/2008 |
| WO | 2008116131 A2 | 9/2008 |
| WO | 2009058207 A1 | 5/2009 |
| WO | 2010078150 A1 | 7/2010 |
| WO | 2010147864 A2 | 12/2010 |
| WO | 2011041523 A2 | 4/2011 |
| WO | 2012118677 A1 | 9/2012 |
| WO | 2012118680 A1 | 9/2012 |
| WO | 2012118683 A1 | 9/2012 |

OTHER PUBLICATIONS

Volume III, Photoinitiators for Free Radical Cationic & Anionic Photopolymerization, $2^{nd}$ Edition by J.V. Crivello & K. Dietliker; edited by G. Bradley; John Wiley and Sons; New York; 1998.

The Chemistry of Radical Polymerization, 2nd ed. Moad and Solomon, pp. 472-479, 488-89, 508-514.

Barton, CRC Handbook of Solubility Par., 1st. Ed. 1983, p. 85-87 and using Tables 13, 14.

International Preliminary Report on Patentability, dated Jun. 24, 2014 for PCT Int'l Appln. No. PCT/US2012/070879.

PCT International Preliminary Report on Patentability, dated Jun. 24, 2014, for PCT Int'l Appln. No. PCT/US2012/070890.

PCT International Preliminary Report on Patentability, dated Jun. 24, 2014, for PCT Int'l Appln. No. PCT/US2012/070895.

PCT International Preliminary Report on Patentability, dated Jun. 24, 2014, for PCT Int'l Appln. No. PCT/US2012/070899.

PCT International Preliminary Report on Patentability, dated Jun. 24, 2014, for PCT Int'l Appln. No. PCT/US2012/070906.

PCT International Search Report, dated Mar. 18, 2013, for PCT Int'l Appln. No. PCT/US2012/070879.

PCT International Search Report, dated Apr. 18, 2013, for PCT Int'l Appln. No. PCT/US2012/070890.

PCT International Search Report, dated Mar. 19, 2013, for PCT Int'l Appln. No. PCT/US2012/070895.

PCT International Search Report, dated May 13, 2013, for PCT Int'l Appln. No. PCT/US2012/070899.

PCT International Search Report, dated Mar. 22, 2013, for PCT Int'l Appln. No. PCT/US2012/070906.

* cited by examiner

IONIC SILICONE HYDROGELS

RELATED APPLICATIONS

This application is a continuation in part of U.S. application Ser. No. 13/720,286, filed on Dec. 19, 2012 entitled IONIC SILICONE HYDROGELS, the contents of which are incorporated by reference.

FIELD OF THE INVENTION

The present invention relates to ionic silicone hydrogels having an exceptional balance of properties which are generated by controlling the reaction kinetics of the components of the reaction mixture.

BACKGROUND OF THE INVENTION

Soft contact lenses made from silicone hydrogels offer improved oxygen permeability as compared to soft lenses made from non-silicone materials such as poly(2-hydroxyethyl methacrylate) (HEMA). Initial efforts to make silicone hydrogel contact lenses were hampered by the poor wettability, high modulus, poor clarity, hydrolytic instability or the high cost of raw materials used to make many of these silicone hydrogels. While various solutions have proven somewhat successful for each of these deficiencies, there remains a need for silicone hydrogels that can be made from inexpensive commercially available monomers, and which have excellent wettability (without the need for surface modification), low modulus, good clarity, and desirable oxygen permeability.

Silicone hydrogels formulations containing polymeric wetting agents, such as poly(N-vinylpyrrolidone) (PVP) and acyclic polyamides have been disclosed. However, these polymers are quite large and require the use of special compatibilizing components, which need to be custom manufactured. Examples of compatibilizing components include 2-propenoic acid, 2-methyl-, 2-hydroxy-3-[3-[1,3,3,3-tetramethyl-1-[(trimethylsilyl)oxy]disiloxanyl]propoxy]propyl ester (SiGMA).

An alternative means of forming a wettable silicone hydrogel lens is to incorporate monomeric N-vinylpyrrolidone (NVP) into the monomer mix used to make the silicone hydrogel polymer, typically in amounts of about 25-55% (by weight) of the monomer mix. Such materials have been described in U.S. Pat. Nos. 4,136,250; 4,153,641; 4,260,725 and 6,867,245. The materials described in these references generally incorporate polyfunctional silicone monomers or macromers, that act as crosslinking agents, and thereby increase the modulus of the final polymer. U.S. Pat. No. 4,139,513 discloses that 2-propenoic acid, 2-methyl-, 2-hydroxy-3-[3-[1,3,3,3-tetramethyl-1-[(trimethylsilyl)oxy]disiloxanyl]propoxy]propyl ester (SiGMA) can be used to form lenses from formulations comprising NVP and HEMA. SiGMA is the only source of silicone disclosed. However, because of the relatively low silicone content in those monomers, desirable levels of oxygen permeability in the final polymers are difficult to achieve.

US 2010/0048847 discloses silicone hydrogels made from a blend of a monomethacryloxyalkyl polydimethylsiloxane methacrylate with about 52% NVP, HEMA and TRIS, and using a blend of ethanol and ethyl acetate as a diluent. The polymers disclosed are (to varying degrees) hazy, but it was disclosed in this application that the haziness could be reduced by the addition of at least about 1.5% methacrylic acid (MAA).

Addition of anionic monomers such as MAA can, however, cause hydrolytic instability in silicone hydrogels, as was disclosed in "The role of ionic hydrophilic monomers in silicone hydrogels for contact lens application", Lai, Y., Valint, P., and Friends, G.; 213th ACS National Meeting, San Francisco, Apr. 13-17, 1997. For this reason, it remains desirable to form clear, hydrolytically stable, wettable (without surface treatment) silicone hydrogels with low moduli from a combination of a monomethacryloxyalkyl polydimethylsiloxane methacrylate such as mPDMS, and NVP.

SUMMARY OF THE INVENTION

The present invention relates to a silicone hydrogel comprising at least one pharmaceutical or nutriceutical component wherein said silicone hydrogel is formed from a reaction mixture comprising about 37 to about 75 wt % of a mixture of slow-reacting hydrophilic monomers, each having a slow-reacting hydrophilic monomer kinetic half life; said mixture of slow reacting hydrophilic monomers comprising and least one slow-reacting ionic monomer;

at least one silicone-containing component having a silicone-containing component kinetic half life, which may be optionally substituted with at least one hydroxyl containing group; and at least one hydroxyl-containing component selected from said silicone-containing components substituted with at least one hydroxyl containing group, at least one hydroxyalkyl monomer, and mixtures thereof, wherein ratio of each of said slow-reacting hydrophilic component half lives to said silicone-containing component half life is at least 2.

The silicone hydrogels of the present invention are useful for making biomedical devices, ophthalmic devices, and particularly contact lenses.

DETAILED DESCRIPTION OF THE INVENTION

Figure 1:
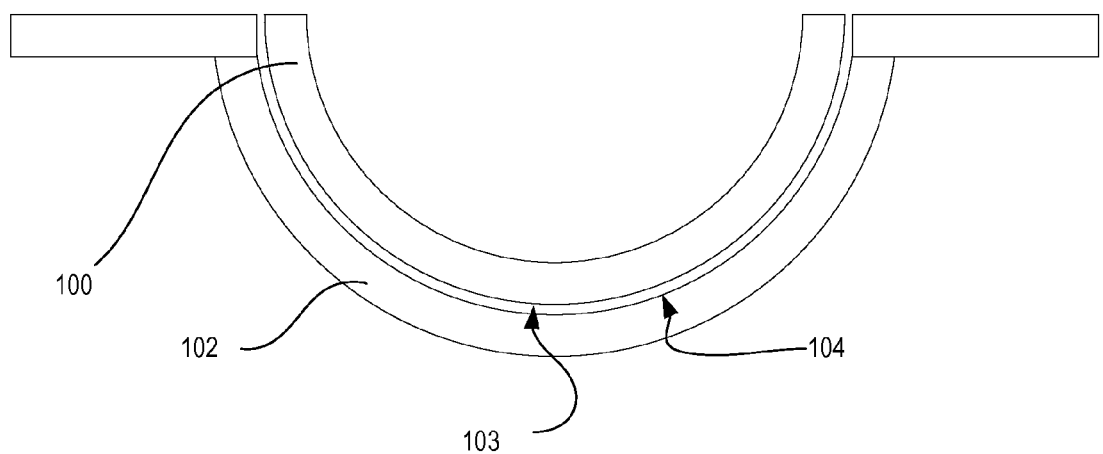
FIG. 1 is a schematic of a lens assembly.

The present invention relates to ionic silicone hydrogels formed from reaction mixtures comprising at least one hydrophilic component and ionic component which have a kinetic half life which is at least twice as long as the kinetic half life of the slowest silicone containing composition. At least one component of the reaction mixture comprises at least one hydroxyl group. The resulting silicone hydrogels are surprisingly easy to process, and display an exceptional balance of properties including stability, haze, water content and oxygen permeability. By introducing an ionic component, and particularly an anionic component into to reactive mixture as a slow reacting component, ionic silicone hydrogels with good stability and a desirable uptake profile can be produced.

The silicone hydrogel polymers of the present invention display stable modulus. As used herein, stable modulus are those which increase less than about 30%, and in some embodiments less than about 20% over 1, 3, 6 or 9 sterilization cycles (121° C. and 30 minutes).

As used herein, "diluent" refers to a non-reactive solvent for the reactive components. Diluents do not react to form part of the biomedical devices.

As used herein, a "biomedical device" is any article that is designed to be used while either in or on mammalian tissues or fluid, and in one embodiment in or on human tissue or fluids. Examples of these devices include but are not limited to catheters, implants, stents, and ophthalmic devices such as intraocular lenses, punctal plugs and contact lenses. The biomedical devices may be ophthalmic devices, particularly contact lenses, most particularly contact lenses made from silicone hydrogels.

As used herein, the terms "ophthalmic device" refers to products that reside in or on the eye. As used herein, the terms "lens" and "ophthalmic device" refer to devices that reside in or on the eye. These devices can provide optical correction, wound care, drug delivery, diagnostic functionality, cosmetic enhancement or effect, glare reduction, UV blocking or a combination of these properties. Non-limiting examples of ophthalmic devices include lenses, punctal plugs and the like. The term lens (or contact lens) includes but is not limited to soft contact lenses, hard contact lenses, intraocular lenses, overlay lenses, ocular inserts, and optical inserts.

As used herein "reaction mixture" refers to reactive and non-reactive components (including the diluent) that are mixed together and reacted to form the silicone hydrogels of the present invention. The reactive components are everything in the reaction mixture except the diluent and any additional processing aids which do not become part of the structure of the polymer. As used herein "(meth)" refers to an optional methyl substitution. Thus, a term such as "(meth) acrylate" denotes both methacrylic and acrylic radicals.

All percentages in this specification are weight percentages unless otherwise noted.

As used herein, the phrase "without a surface treatment" or "not surface treated" means that the exterior surfaces of the devices of the present invention are not separately treated to improve the wettability of the device. Treatments which may be foregone because of the present invention include, plasma treatments, grafting, coating and the like. Coatings which provide properties other than improved wettability, such as, but not limited to antimicrobial coatings and the application of color or other cosmetic enhancement, are not considered surface treatment.

As used herein "silicone macromers" and silicone "prepolymers" mean mono- and multi-functional silicone containing compounds having molecular weights of greater than about 2000.

As used herein "hydroxyl-containing component" is any component containing at least one hydroxyl group.

As used herein "kinetic half life" means the time elapsed at the given reaction conditions for 50% of the reactive component to be consumed. It should be appreciated that the kinetic half life for a given component will be influenced by the other reaction mixture components, as well as the cure conditions selected, as is described in detail herein. Kinetic half life is calculated as described in the examples.

The kinetic half life ratios calculated herein must be calculated using the kinetic half lives measured from that particular reaction mixture and cure conditions.

As used herein "monovalent reactive groups" are groups that can undergo free radical and/or cationic polymerization. Non-limiting examples of free radical reactive groups include (meth)acrylates, styryls, vinyls, vinyl ethers, $C_{1-6}$alkyl(meth)acrylates, (meth)acrylamides, $C_{1-6}$alkyl(meth)acrylamides, N-vinyllactams, N-vinylamides, $C_{2-12}$alkenyls, $C_{2-12}$alkenylphenyls, $C_{2-12}$alkenylnaphthyls, $C_{2-6}$alkenylphenyl$C_{1-6}$alkyls, O-vinylcarbamates and O-vinylcarbonates. Non-limiting examples of cationic reactive groups include vinyl ethers or epoxide groups and mixtures thereof. Non-limiting examples of free radical reactive groups include (meth)acrylate, acryloxy, (meth)acrylamide, and mixtures thereof.

As used herein "ionic" components include anionic components, cationic components, zwitterionic components and mixtures thereof. Ionic components include salts of ionic compounds and precursors which can be converted to ionic form via protonation, deprotonation or mild hydrolysis, such as azalactones disclosed in U.S. Pat. No. 4,810,764 and U.S. Pat. No. 6,902,812, which are converted to amino acids via hydrolysis.

In the present invention the components are selected to react at specific points in the reaction. For example, "fast reacting" components are selected to polymerize primarily at the beginning of the overall copolymerization reaction, while the slow reacting hydrophilic monomer is selected to polymerize primarily at the end of the overall copolymerization reaction. Fast reacting components include the silicone-containing components, the hydroxyalkyl monomers and some crosslinkers. In one embodiment slow reacting components have kinetic half lives which are at least about two times greater than the fastest silicone containing monomer. Kinetic half lives may be measured as described herein. It should be appreciated that the kinetic half lives are relative to specific formulations.

Examples of slow reacting groups include (meth)acrylamides, vinyls, allyls and combinations thereof and a least one hydrophilic group. Non-limiting examples of the slow reacting group include from N-vinyl amides, O-vinyl carbamates, O-vinyl carbonates, N-vinyl carbamates, O-vinyl ethers, O-2-propenyl, wherein the vinyl or allyl groups may be further substituted with a methyl group. The slow reacting group may be selected from N-vinyl amides, O-vinyl carbonates, and O-vinyl carbamates.

Examples of fast reacting groups include (meth)acrylates, styryls, (meth)acryamides and mixtures thereof. Generally (meth)acrylates are faster than (meth)acrylamides, and acrylamides are faster than (meth)acrylamides.

Throughout the specification, wherever chemical structures are given, it should be appreciated that alternatives disclosed for the substituents on the structure may be combined in any combination. Thus if a structure contained substituents $R_1$ and $R_2$, each of which contained three lists of potential groups, 9 combinations are disclosed. The same applies for combinations of properties.

It has been surprisingly found that by selecting the components of the reaction mixture, silicone hydrogels having a desirable balance of properties many be formed. The reaction mixtures of the present invention comprise about 37 to about 75 wt %, in some embodiments between about 39 and about 70 wt % and in other embodiments between about 39 and about 60 wt % of at least one slow-reacting hydrophilic monomer;

at least one reactive silicone-containing component;

and at least one fast reacting crosslinker having at least two fast reacting groups. The slowest reacting silicone-containing component has a kinetic half life which is at least half the kinetic half life of the slow-reacting hydrophilic monomer. At least one of said components comprises at least one hydroxyl group.

The first component of the reactive mixture is at least one slow-reacting hydrophilic monomer. The slow-reacting hydrophilic monomer comprises a slow reacting group and a least one hydrophilic group. The reactive group may be selected from N-vinyl amides, O-vinyl carbamates, O-vinyl carbonates, N-vinyl carbamates, O-vinyl ethers, O-2-propenyl, wherein the vinyl or allyl groups may be further substituted with a methyl group. In yet another embodiment the reactive group is selected from N-vinyl amides, O-vinyl carbonates and O-vinyl carbamates. Hydrophilic groups include hydroxyls, amines, ethers, amides, ammonium groups, carboxylic acid, carbamates, combinations thereof and the like. Suitable hydrophilic groups include hydroxyls, ethers, amides, carboxylic acid combinations thereof and the like.

If a (meth)acrylamide is selected as the slow-reacting hydrophilic monomer, a silicone-containing monomer having a very short kinetic half life, such as an acrylate must be used. Methacrylamides are generally slower reacting that acrylamides, and bulky (meth)acrylamides are slower than smaller (meth)acrylamides. Examples of a suitable (meth)acrylamide include bis-(2-hydroxyethyl) methacrylamide, 2,3-dihydroxypropyl methacrylamide, N-[3-(Dimethylamino)propyl]methacrylamide, N-[tris(hydroxymethyl)methyl]acrylamide and methacrylamides substituted with one or two polyethylene glycol chains having 2-10, 2-5 repeating units and the like. Where a methacrylamide is used as the slow-reacting hydrophilic monomer, very fast silicone containing monomer, such as silicone acrylates should be used to provide the desired difference in kinetic half lives. For example, N-[3-(Dimethylamino)propyl]methacrylamide may be used as the slow-reacting hydrophilic monomer with silicone acrylates.

In another embodiment the slow-reacting hydrophilic monomer is selected from N-vinylamide monomer of Formula I, a vinyl pyrrolidone of Formula II-IV, n-vinyl piperidone of Formula V:

Formula I
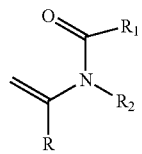

Formula II
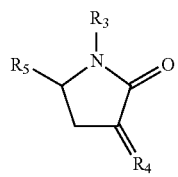

Formula III
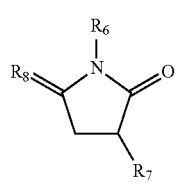

Formula IV
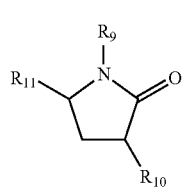

Formula V
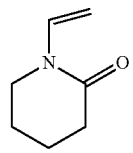

wherein R is H or methyl, and in one embodiment R is H;

$R_1$, $R_2$, $R_3$, $R_6$, $R_7$, $R_{10}$, and $R_H$ are independently selected from H, $CH_3$, $CH_2CH_3$, $CH_2CH_2CH_3$, $C(CH_3)_2$;

$R_4$ and $R_8$ are independently selected from $CH_2$, $CHCH_3$ and $—C(CH_3)$;

$R_5$ is selected from H, methyl, ethyl; and $R_9$ is selected from $CH=CH_2$, $CCH_3=CH_2$, and $CH=CHCH_3$.

In one embodiment the total number of carbon atoms in $R_1$ and $R_2$ is 4 or less, and in another embodiment $R_1$ and $R_2$ are methyl.

In another embodiment the slow-reacting hydrophilic monomer is selected from the N-vinyl amide monomer of Formula I or a vinyl pyrrolidone of Formula II or IV. In yet another embodiment $R_6$ is methyl, $R_7$ is hydrogen, $R_9$ is $CH=CH_2$, $R_{10}$ and $R_{11}$ are H.

In another embodiment the slow-reacting hydrophilic monomer is selected from ethylene glycol vinyl ether (EGVE), di(ethylene glycol) vinyl ether (DEGVE), N-vinyl lactams, including N-vinyl pyrrolidone (NVP), 1-methyl-3-methylene-2-pyrrolidone, 1-methyl-5-methylene-2-pyrrolidone, 5-methyl-3-methylene-2-pyrrolidone; 1-ethyl-5-methylene-2-pyrrolidone, N-methyl-3-methylene-2-pyrrolidone, 5-ethyl-3-methylene-2-pyrrolidone, 1-n-propyl-3-methylene-2-pyrrolidone, 1-n-propyl-5-methylene-2-pyrrolidone, 1-isopropyl-3-methylene-2-pyrrolidone, 1-isopropyl-5-methylene-2-pyrrolidone, N-vinyl-N-methyl acetamide (VMA), N-vinyl-N-ethyl acetamide, N-vinyl-N-ethyl formamide, N-vinyl formamide, N-vinyl acetamide, N-vinyl isopropylamide, allyl alcohol, N-vinyl caprolactam, N-2-hydroxyethyl vinyl carbamate, N-carboxyvinyl-β-alanine (VINAL), N-carboxyvinyl-α-alanine and mixtures thereof.

In another embodiment the slow-reacting hydrophilic monomer is selected from NVP, VMA and 1-methyl-5-methylene-2-pyrrolidone. In yet another embodiment the slow-reacting hydrophilic monomer comprises NVP.

The reactive mixture further comprises at least one slow reacting ionic component. The ionic component may be cationic, anionic or zwitterionic.

Suitable reactive groups for the ionic components include N-vinyl amides, O-vinyl carbamates, O-vinyl carbonates, N-vinyl carbamates, O-vinyl ethers, O-2 propenyl, wherein the vinyl or allyl groups may be further substituted with a methyl group and in some embodiments methacrylamide reactive groups. Preferred reactive groups include vinyl ethers, vinyl carbamates, vinyl carbonates, and vinyl amides. The anionic components also comprise at least one anionic group selected from carboxylic acids, sulfonic acids, boronic acids, phosphonics acids, and their salts, oxazolones and mixtures thereof.

Examples of anionic components include 4-acrylamidobutanoic acid (ACA1I), (3-acrylamidophenyl)boronic acid (APBA), 3-acrylamidopropionic acid, 5-acrylamidopentanoic acid, 3-acrylamido-3-methylbutanoic acid (AMBA), N-vinyloxycarbonyl-α-alanine, N-vinyloxycarbonyl-β-alanine (VINAL), 2-vinyl-4,4-dimethyl-2-oxazolin-5-one (VDMO), reactive sulfonate salts, including, vinyl sulphonate sodium salt, vinyl sulphonate salt, acetic acid, 2-carboxymethoxy)-, 1-ethenylester, of Formula

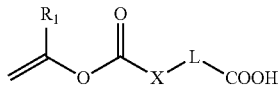

Where $R_1$ is H or methyl, X is O or $NR_{16}$, $R_{16}$ is H or $C_{1-3}$ alkyl), and L is divalent $C_{1-4}$ alkyl group; and mixtures thereof.

In one embodiment the slow-reacting anionic component is selected from the group consisting of N-vinyloxycarbonyl-α-alanine; N-vinyloxycarbonyl-β-alanine (VINAL); 2-vinyl-4,4-dimethyl-2-oxazolin-5-one (VDMO); vinyl sulphonate sodium salt; acetic acid, 2-(carboxymethoxy)-, 1-ethenylesters of the above Formula, mixtures thereof and the like.

Suitable cationic components include slow reacting components having a positive charge. Cationic groups include amino and ammonium groups. Examples of slow reacting cationic components include allyl amine.

Zwitterioinic components contain both a cationic and anionic charge in the same molecule. Suitable zwitterionic groups include amino acids, ammonium carboxylates, ammonium sulfonate, and phospholipids. Examples include 3-((3-methacrylamidopropyl)dimethylammonio)propane-1-sulfonate (MAMPDAPS); 3-((3-acrylamidopropyl)dimethylammonio)propane-1-sulfonate (AMPDAPS), vinyl carbonate or vinyl carbamates substituted with at least one group selected from amino, ammonium, ammonium sulfonate, ammonium carboxylate and phosphadityl sulfonate, combinations thereof and the like.

The ionic components are present in the reactive mixture in an amount below about 20 mole %, 15 mole %, between about 0.5 and about 10 mole %, between about 0.5 and about 5 mole %, based upon all components in the reaction mixture.

In one embodiment, all of the slow-reacting components have the same reactive functionality, and in one embodiment vinyl functionality.

The slow reacting hydrophilic monomers are present in amounts to provide wettability to the resulting polymer. Wettability may be measured via contact angle, and desirable contact angles are less than about 80°, less than about 70° and in some embodiments less than about 60°.

The at least one silicone-containing monomer is monofunctional and comprises (a) a fast reacting group and (b) a polydialkyl siloxane chain. In another embodiment the silicon-containing monomer comprises a fast reacting group selected from (meth)acrylates, styryls, (meth)acrylamides and mixtures thereof. The at least one silicone-containing monomer may also contain at least one fluorine. In yet another embodiment the silicone-containing component is selected from mono (meth)acryloxyalkyl polydialkylsiloxane monomer of Formula VII or the styryl polydialkylsiloxane monomer of Formula VIII:

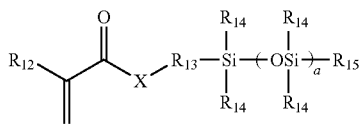

Formula VII

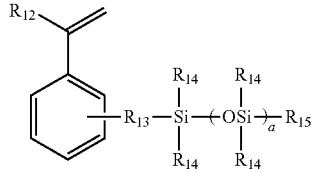

Formula VIII wherein $R_{12}$ is H or methyl;

X is O or $NR_{16}$,

Each $R_{14}$ is independently a phenyl or $C_1$ to $C_4$ alkyl which may be substituted with fluorine, hydroxyl or ether, and in another embodiment each $R_{14}$ is independently selected from ethyl and methyl groups, and in yet another embodiment, all $R_{14}$ are methyl;

$R_{15}$ is an unsubstituted $C_1$ to $C_4$ alkyl;

$R_{13}$ is a divalent alkyl group, which may further be functionalized with a group selected from the group consisting of ether groups, hydroxyl groups, carbamate groups and combinations thereof, and in another embodiment $C_1$-$C_6$ alkylene groups which may be substituted with ether, hydroxyl and combinations thereof, and in yet another embodiment $C_1$ or $C_3$-$C_6$ alkylene groups which may be substituted with ether, hydroxyl and combinations thereof;

a is 2 to 50, and in some embodiments 5 to 15.

$R_{16}$ is selected from H, $C_{1-4}$ alkyls, which may be further substituted with one or more hydroxyl groups, and in some embodiments is H or methyl.

In yet another embodiment $R_{12}$ and each $R_{14}$ are methyl.

In yet another embodiment at least one $R_{14}$ is 3,3,3-trifluoropropyl.

Examples of suitable silicone-containing monomers include monomethacryloxyalkylpolydimethylsiloxane methacrylates selected from the group consisting of monomethacryloxypropyl terminated mono-n-butyl terminated polydimethylsiloxane, monomethacryloxypropyl terminated mono-n-methyl terminated polydimethylsiloxane, monomethacryloxypropyl terminated mono-n-butyl terminated polydiethylsiloxane, monomethacryloxypropyl terminated mono-n-methyl terminated polydiethylsiloxane, N-(2,3-dihydroxypropane)-N'-(propyl tetra(dimethylsiloxy) dimethylbutylsilane)acrylamide, α-(2-hydroxy-1-methacryloxypropyloxypropyl)-ω-butyl-decamethylpentasiloxane, and mixtures thereof.

In another embodiment the silicone-containing component is selected from the group consisting of monomethacryloxypropyl terminated mono-n-butyl terminated polydimethylsiloxane, monomethacryloxypropyl terminated mono-n-methyl terminated polydimethylsiloxane, N-(2,3-dihydroxypropane)-N'-(propyl tetra(dimethylsiloxy) dimethylbutylsilane)acrylamide, α-(2-hydroxy-1-methacryloxypropyloxypropyl)-w-butyl-decamethylpentasiloxane, and mixtures thereof.

In another embodiment the silicone containing component is selected from acrylamide silicones of US20110237766, and particularly the silicone monomers expressed in the following general formulae (s1) through (s6).

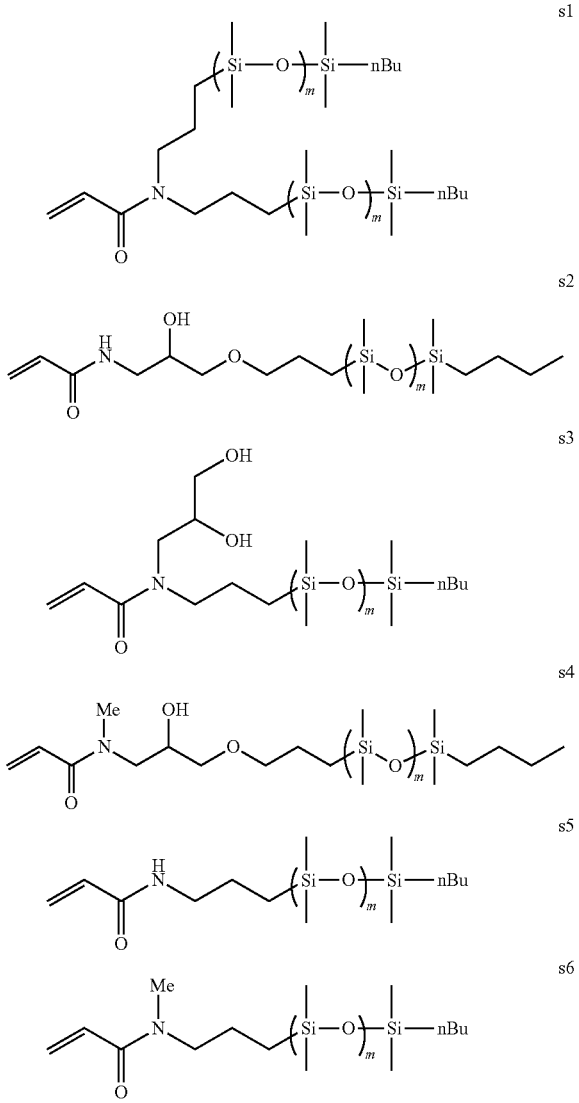

wherein m is 4-12 and in some embodiments 4-10.

Additional silicone containing components having one or more polymerizable groups may also be included. Any additional disclosed silicone components having the herein disclosed reactive groups may be included. Examples include silicone containing monomers displaying branched siloxane chains such as SiMAA and TRIS. Because the anionic components are slow reacting, the silicone hydrogels of the present invention may comprise fast reacting silicones comprising trimethylsiloxy siloxane (TMS) groups, such as SiMAA and TRIS, even in relatively large amounts up to about 20 wt %. However, neither SiMAA nor TRIS are effective as the main silicone containing component where oxygen permeabilities of greater than about 70 or 80 Dk are desired. Accordingly, in one embodiment the amount of TRIS in the formulation is less than about 15%, 10% and less than 5%. Some embodiments contain no TRIS.

The at least one silicone-containing component is present in the reactive mixture in an amount sufficient to provide the desired oxygen permeability. It is a benefit of the present invention that oxygen permeabilities greater than about 70 barrers, greater than about 80 barrer, in some embodiments greater than about 90 barrer, and in other embodiments greater than about 100 barrer may be achieved. Suitable amounts will depend on the length of the siloxane chain included in the silicone-containing monomers, with silicone-containing monomers having longer chains requiring less monomer. Amounts include from about 20 to about 60 weight %, and in some embodiments from about 30 to about 55 weight %.

In one embodiment the total amount of silicon in the reactive mixture (excluding diluent) is between about 9 and 14 wt % and between about 9 and 13%. Limiting the amount of silicon, in combination balancing the amount of the slow-reacting hydrophilic monomer and the other reactive components, provides the desirable combination of properties achieved by the present invention. It is a benefit of the present application that silicone hydrogels having the combination oxygen permeabilities and water contents may be formed with only moderate amounts (less than 14 wt %) silicon.

The slow-reacting hydrophilic monomer and the at least one silicone-containing monomer are selected such that the ratio of the kinetic half life of the slow-reacting hydrophilic monomer to the kinetic half life of the slowest silicone-containing component is at least about 2, at least about 3 and in some embodiments at least about 5.

As part of the present invention it is desirable to polymerize long chains of the slow-reacting hydrophilic monomer. A substantial amount of slow-reacting hydrophilic monomer must polymerize late in the process in order to achieve the desired balance of properties. In one embodiment this is characterized by the ratio (unit-less) of the concentrations (expressed in µmol/g) of the slow-reacting hydrophilic monomer to the slowest reacting silicone-containing monomer at 90% conversion of the slowest reacting silicone-containing monomer ("conversion ratio"). In one embodiment the conversion ratio is greater than about 10, at least about 20, and in other embodiments at least about 30.

In one embodiment the reaction mixture is substantially free of TRIS, and in another is substantially free of silicone containing macromers or prepolymers.

At least one of the components of the reaction mixture must contain at least one hydroxyl group. The hydroxyl may be contained on the silicone-containing monomer, an additional monomer or a combination thereof. It is preferred that the kinetic half life of the hydroxyl-containing component be close to the kinetic half life of the silicone containing monomers. Preferred kinetic half life ratios of the hydroxyl-containing component to the silicone containing monomer include about 0.75 to about 1.5 and about 0.8 to 1.2. In one embodiment, the hydroxyl containing components have the same reactive functionality as the silicone-containing monomers.

Also, (meth)acrylate monomers with hydroxyl group(s), such as but not limited to SiMAA, and HEMA, have been found to be better at compatibilizing NVP, VMA and other amide containing monomers, than (meth)acrylamide monomers with hydroxyl group(s). Thus in one embodiment where clear lenses with dynamic advancing contact angles of less than about 80° are desired, the hydroxyl-containing monomers comprising (meth)acrylate monomers.

The hydroxyl-containing components may be present in mole percents which form a molar ratio of hydroxyl groups to the slow-reacting hydrophilic monomer of at least about 0.15 and in some embodiments between about 0.15 and about 0.4. This is calculated by dividing the number of moles of hydroxyl groups in the hydroxyl group-containing monomers (including any hydroxyl groups on the slow-reacting hydrophilic monomer and the silicone-containing monomer) by the number of moles of the slow-reacting hydrophilic monomer per a given mass of the monomer mix. In this embodiment, for a reaction mixture comprising HO-mPDMS, HEMA, EGVE and NVP, the hydroxyl groups on each of HO-mPDMS, HEMA and EGVE would be counted. Any hydroxyl groups present in the diluent (if used) are not included in the calculation. In one embodiment at least one silicone-containing monomer comprises at least one hydroxyl group.

Alternatively, the molar ratio of all hydroxyl groups on reaction components in the reaction mixture to silicon (HO: Si) is between about 0.16 and about 0.4. The molar ratio is calculated by dividing molar concentration of hydroxyl groups in the components of the reactive mixture (other than any hydroxyls which are part of the slow-reacting hydrophilic monomer or diluents) by the molar concentration of silicon. In this embodiment both the hydroxyalkyl monomers and any hydroxyl-containing silicone components are included in the calculation. Thus, in calculating the HO:Si ratio of the reaction mixture comprising HO-mPDMS, HEMA, NVP and EGVE, only the hydroxyl groups on each of HO-mPDMS, HEMA would be counted in calculating the HO:Si.

In another embodiment the molar ratio of hydroxyl groups in non-silicone containing components (other than any hydroxyls which are part of the slow-reacting hydrophilic monomer or diluents) to silicon is between about 0.13 and about 0.35. Thus, in calculating the $HO_{non-Si}$:Si ratio of the reaction mixture comprising HO-mPDMS, HEMA, EGVE, and NVP only the hydroxyl groups on, HEMA would be counted in calculating the $HO_{non-Si}$:Si ratio.

It will be appreciated that the minimum amount of hydroxyl component will vary depending upon a number of factors, including, the number of hydroxyl groups on the hydroxyalkyl monomer, the amount, molecular weight and presence or absence of hydrophilic functionality on the silicone containing components. For example, where HEMA is used as the hydroxyalkyl monomer and mPDMS is used in amounts about 38 wt % as the sole silicone containing monomer, at least about 8 wt % HEMA (0.16 HO:Si) is included to provide the desired haze values. However, when lesser amounts of mPDMS are used (about 20%), as little as about 2 or 3% HEMA provides silicone hydrogel contact lenses having haze values below about 50%. Similarly, when the formulation includes substantial amounts of a hydroxyl-containing silicone component (such as greater than about 20 wt % HO-mPDMS), amounts of HEMA as low as about 7 wt % (0.13 HO:Si, or 0.24 $HO_{total}$:Si) may provide the desired level of haze.

Suitable hydroxyl-containing monomers include hydroxyalkyl (meth)acrylate or (meth)acrylamide monomer of Formula IX or a styryl compound of Formula X:

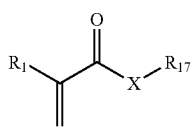

FORMULA IX

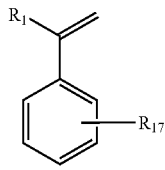

FORMULA X wherein $R_1$ is H or methyl,
X is O or $NR_{16}$, $R_{16}$ is a H, $C_1$ to $C_4$ alkyl, which may be further substituted with at least one OH, in some embodiments methyl or 2-hydroxyethyl and $R_{17}$ is selected from $C_2$-$C_4$ mono or dihydroxy substituted alkyl, and poly(ethylene glycol) having 1-10 repeating units; and in some embodiments 2-hydroxyethyl, 2,3-dihydroxypropyl, 2-hydroxypropyl.

In one embodiment $R_1$ is H or methyl, X is oxygen and R is selected from $C_2$-$C_4$ mono or dihydroxy substituted alkyl, and poly(ethylene glycol) having 1-10 repeating units. In another embodiment $R_1$ methyl, X is oxygen and R is selected from $C_2$-$C_4$ mono or dihydroxy substituted alkyl, and poly (ethylene glycol) having 2-20 repeating units, and in yet another embodiment $R_1$ methyl, X is oxygen and R is selected from $C_2$-$C_4$ mono or dihydroxy substituted alkyl. In one embodiment, at least one hydroxyl group is on the terminal end of the R alkyl group.

Examples of suitable hydroxyalkyl-containing monomers include 2-hydroxyethyl methacrylate, 2-hydroxyethyl acrylate, 3-hydroxypropyl (meth)acrylate, 2-hydroxypropyl (meth)acrylate, 1-hydroxypropyl-2-(meth)acrylate, 2-hydroxy-2-methyl-propyl (meth)acrylate, 3-hydroxy-2,2-dimethyl-propyl (meth)acrylate, 4-hydroxybutyl (meth)acrylate, glycerol (meth)acrylate, 2-hydroxyethyl (meth)acrylamide, polyethyleneglycol monomethacrylate, bis-(2-hydroxyethyl) (meth)acrylamide, 2,3-dihydroxypropyl (meth)acrylamide, and mixtures thereof.

In another embodiment the hydroxyl-containing monomer is selected from the group consisting of 2-hydroxyethyl methacrylate, glycerol methacrylate, 2-hydroxypropyl methacrylate, hydroxybutyl methacrylate, 3-hydroxy-2,2-dimethyl-propyl methacrylate, and mixtures thereof.

In yet another embodiment the hydroxyl-containing monomer comprises 2-hydroxyethyl methacrylate, and in another embodiment comprises 3-hydroxy-2,2-dimethyl-propyl methacrylate. In an alternate embodiment the hydroxyl-containing monomer comprises glycerol methacrylate.

The reactive mixture may further comprise additional hydrophilic monomers. Any hydrophilic monomers used to prepare hydrogels may be used. For example monomers containing acrylic groups ($CH_2$=CROX, where R is hydrogen or $C_{1-6}$alkyl an X is O or N) or vinyl groups (—C=$CH_2$) may be used. Examples of additional hydrophilic monomers are N,N-dimethylacrylamide, polyethyleneglycol monomethacrylate, methacrylic acid, acrylic acid, combinations thereof and the like.

If the additional hydrophilic monomers have kinetic half lives which are intermediate to the slow reacting hydrophilic monomers and silicone containing components as defined herein, their concentrations in the formulations of the present invention may be limited to concentrations which do not provide the lens with an advancing contact angle higher than about 80°. As used herein, "intermediate" half life is one that is between 20% and 70% faster than the slowest reacting silicone component. For example, if the additional hydrophilic monomer is N,N-dimethylacrylamide, the amount of the additional hydrophilic monomer is limited to below about 3 wt % in cases where uncoated lenses are desired. Where the lens is to be surface modified, higher amounts of additional monomers may be included.

The reaction mixtures of the present invention further comprise at least one crosslinker which has a kinetic half life less than or equal to the kinetic half life of at least one of the silicone-containing monomers included in the reaction mixture. A crosslinker is a monomer with two or more polymerizable double bonds. It has been found that when the kinetic half life of the crosslinker is longer than at least one of the silicone-containing monomers, the resulting hydrogel displays decreased modulus and increased water content. Surprisingly, the reaction rate of the crosslinker can be substantially reduced by the inclusion of a UV absorbing compound. This increases the kinetic half life, and in some systems changed the reaction order, such that the crosslinker reacted more slowly that the silicone-containing monomers. In this circumstance it may be desirable to use a crosslinker with a faster reaction rate in the presence of the selected UV absorber.

Suitable crosslinkers include ethylene glycol dimethacrylate ("EGDMA"), trimethylolpropane trimethacrylate ("TMPTMA"), glycerol trimethacrylate, polyethylene glycol dimethacrylate (wherein the polyethylene glycol preferably has a molecular weight up to, e.g., about 5000), and other polyacrylate and polymethacrylate esters, such as the end-capped polyoxyethylene polyols described above containing two or more terminal methacrylate moieties. The crosslinker may be used in the usual amounts, e.g., from about 0.000415 to about 0.0156 mole per 100 grams of reactive components in the reaction mixture. Alternatively, if the hydrophilic monomers and/or the silicone containing monomers act as the cross-linking agent, the addition of an additional crosslinking agent to the reaction mixture is optional. Examples of hydrophilic monomers which can act as the crosslinking agent and when present do not require the addition of an additional crosslinking agent to the reaction mixture include polyoxyethylene polyols described above containing two or more terminal methacrylate moieties.

An example of a silicone containing monomer which can act as a crosslinking agent and, when present, does not require the addition of a crosslinking monomer to the reaction mixture includes α,ω-bismethacryloypropyl polydimethylsiloxane.

The reaction mixtures can also contain multiple crosslinkers depending on the reaction rate of the hydrophilic component. With very slow reacting hydrophilic components (e.g. VMA, EGVE, DEGVE) crosslinkers having slow reacting functional groups (e.g. di-vinyl, tri-vinyl, di-allyl, tri-allyl) or a combination of slow reacting functional groups and fast reacting functional groups (e.g. HEMAVc, allylmethacrylate) can be combined with crosslinkers having fast reacting functional groups to improve the retention of the polymers of the slow-reacting monomers in the final hydrogel.

In one embodiment the reaction mixture comprises at least two crosslinkers, at least one fast reacting crosslinker having at least two fast reacting groups which will react with the silicone components and hydroxyl-containing components and at least one slow reacting crosslinker having at least two slow reacting groups which react with the slow reacting hydrophilic monomer. This mixture of fast and slow reacting crosslinkers provides the final polymer with improved resilience and recovery, particularly on the surface of the lens. Examples of suitable first crosslinkers include those having only (meth)acrylate functionality, such as EGDMA, TEGDMA and combinations thereof. Examples of suitable second crosslinkers include those having only vinyl functionality, such as triallyl cyanurate (TAC). When mixtures are used, suitable amounts of all crosslinker in the reactive mixture include between about 0.10% and about 2%, or between about 0.10% and about 1%, excluding diluent respectively. In another embodiment the total amount of all crosslinker in the reactive mixtures is between 0.7 to about 6.0 mmol/100 g of polymerizable components; between about 0.7 to about 4.0 mmoles per 100 g of reactive components. The fast and slow reacting crosslinkers are present in respective amounts of about 0.3 to about 2.0 mmol/100 g of polymerizable components; or between about 0.4 to about 2.0 mmoles per 100 g of reactive components.

The reaction mixture may also comprise at least one UV absorbing compound. Surprisingly, UV absorbing compounds can have a substantially different impact on the reaction kinetics of the reactive components in the reaction mixtures of the present invention. For example, it has been found that benzotriazoles substantially slow the rate of reaction for NVP and TEGDMA is some systems much more than the reaction rates of the silicone-containing components. In the case of NVP, this is beneficial, as it provides additional processing flexibility and an exceptional balance of properties, including water contents in excess of about 60%, haze values less than about 50%, less than about 10%, advancing contact angles less than about 60° and Dk's greater than about 80. When the silicone hydrogel will be used as an ophthalmic device it may be desirable to incorporate a reactive UV absorbing compound in the reaction mixture so that the resulting silicone hydrogel will be UV absorbing. However, in another embodiment non-reactive UV absorbing compounds may be used solely to achieve the desired reaction kinetics. Alternatively solution filters may be used. It is believed that the UV absorbers in the reactive mixtures block incident light below about 370 nm which alters the spectrum of light being imposed on the visible photoinitiator. This tends to reduce the rate of initiation as well as lower the concentration of initiator radicals present, which in turn is believed to have a significant impact on the rate of polymerization of the monomers. Typically, the monomers which are likely to be most significantly impacted are the slowest and fastest. In several of the examples included herein, NVP (slowest) and TEGDMA (the fastest) are the most sensitive to the presence of the UV absorber.

Suitable UV absorbers may be derived from 2-(2'-hydroxyphenyl)benzotriazoles, 2-hydroxybenzophenones, 2-hydroxyphenyltriazines, oxanilides, cyanoacrylates, salicylates and 4-hydroxybenzoates; which may be further reacted to incorporate reactive polymerizable groups, such as (meth) acrylates. Specific examples of UV absorbers which include polymerizable groups include 2-(2'-hydroxy-5-methacryloxyethylphenyl)-2H-benzotriazole (Norbloc), 5-vinyl and 5-isopropenyl derivatives of 2-(2,4-dihydroxyphenyl)-2H-benzotriazole and 4-acrylates or 4-methacrylates of 2-(2,4-dihydroxyphenyl)-2H-benzotriazole or 2-(2,4-dihydroxyphenyl)-1,3-2H-dibenzotriazole, mixtures thereof and the like. When a UV absorber is included, it may be included in amounts between about 0.5 and about 4 wt %, and suitably between about 1 wt % and about 2 wt %.

A polymerization initiator is preferably included in the reaction mixture. Either thermal, photoinitiation or a combination thereof may be used. In one embodiment, the reaction mixtures of the present invention comprise at least one photoinitiator. The use of photoinitiation provides desirable cure times (time to reach essentially complete cure) of less than about 30 minutes, less than about 20 minutes or less than about 15 minutes. The photopolymerization systems also greater flexibility in tailoring the properties of the resulting silicone hydrogel through the use of UV absorbers in the reaction mixtures. Suitable photoinitiator systems include aromatic alpha-hydroxy ketones, alkoxyoxybenzoins, acetophenones, acylphosphine oxides, bisacylphosphine oxides, and a tertiary amine plus a diketone, mixtures thereof and the like. Illustrative examples of photoinitiators are 1-hydroxycyclohexyl phenyl ketone, 2-hydroxy-2-methyl-1-phenyl-propan-1-one, bis(2,6-dimethoxybenzoyl)-2,4-4-trimethylpentyl phosphine oxide (DMBAPO), bis(2,4,6- trimethylbenzoyl)-phenyl phosphineoxide (Irgacure 819), 2,4,6-trimethylbenzyldiphenyl phosphine oxide and 2,4,6-trimethylbenzoyl diphenylphosphine oxide, benzoin methyl ester and a combination of camphorquinone and ethyl 4-(N, N-dimethylamino)benzoate. Commercially available visible light initiator systems include Irgacure 819, Irgacure 1700, Irgacure 1800, Irgacure 819, Irgacure 1850 (all from Ciba Specialty Chemicals) and Lucirin TPO initiator (available from BASF). Commercially available UV photoinitiators include Darocur 1173 and Darocur 2959 (Ciba Specialty Chemicals). These and other photoinitiators which may be used are disclosed in Volume III, Photoinitiators for Free Radical Cationic & Anionic Photopolymerization, $2^{nd}$ Edition by J. V. Crivello & K. Dietliker; edited by G. Bradley; John Wiley and Sons; New York; 1998, which is incorporated herein by reference. Suitable thermal initiators include lauryl peroxide, benzoyl peroxide, isopropyl percarbonate, azobisisobutyronitrile, and the like. The initiator is used in the reaction mixture in effective amounts to initiate polymerization of the reaction mixture, e.g., from about 0.1 to about 2 parts by weight per 100 parts of reactive monomer.

The initiator is used in the reaction mixture in effective amounts to initiate polymerization of the reaction mixture, e.g., from about 0.1 to about 2 parts by weight per 100 parts of reactive monomer. As is shown in the Examples, the concentration of photoinitiator used can affect the reaction kinetics of the reactive components. While increasing the amount of initiator generally decreases the kinetic half live of all the components, the half lives are not affected equally. Thus, the ratio of the slow-reacting hydrophilic monomer and silicone containing monomer can be adjusted by varying the initiator concentration. The effect can be increased by adding or increasing the concentration of inhibitors included in the reactive mixture. Some inhibitors may be included with the monomers which are selected. Inhibitors may also be intentionally added to the reaction mixtures of the present application. The amount of inhibitor which may be included is from about 100 to about 2,500 µgm/gm of reaction mixture.

Inhibitors may optionally be included. Surprisingly the inclusion of even substantial amounts of BHT, a free radical inhibitor did not substantially change the half life ratios measured. However, inclusion of increasing amounts of inhibitor did change the properties of the resulting lenses, decreasing modulus. Thus, it may be desirable to include at least one inhibitor in the reactive mixture. Free radical inhibitors are compounds that react rapidly with propagating radicals to produce stable radical species that terminate the chain. Classes of inhibitors include quinones, substituted phenols, secondary aromatic amines, lactones and nitro compounds. Specific examples of inhibitors include BHT, MEHQ, hydroxyamines, benzofuranone derivatives, molecular oxygen, vitamin E, nitric oxide/nitrogen dioxide mixtures (which form nitroxides in situ) mixtures and combinations thereof and the like.

Examples of classes of chain transfer agents include alkyl thiols, dithiocarboxylic acid esters, combinations thereof and the like. Examples of controlled free radical initiators include nitroxide mediated polymerization (NMP) (including those disclosed in The Chemistry of Radical Polymerization, 2nd ed. Moad and Solomon, pgs 472-479), atom-transfer radical polymerization (ATRP), including low molecular weight activated organic halides (including those disclosed in The Chemistry of Radical Polymerization, 2nd ed. Moad and Solomon, pgs 488-89 and 492-497), and reversible addition fragmentation (chain) transfer (RAFT) polymerization, including thiocarbonylthio agents (such as those disclosed at including those disclosed in The Chemistry of Radical Polymerization, 2nd ed. Moad and Solomon, pgs 508-514). In the case where controlled free radical initiators are used, they are used as part or all of the initiator system.

Polymerization of the reaction mixture can be initiated using the appropriate choice visible or ultraviolet light. Alternatively, initiation can be conducted without a photoinitiator using, for example, e-beam. The initiators may be selected from bisacylphosphine oxides, such as bis(2,4,6-trimethylbenzoyl)-phenyl phosphine oxide (Irgacure 819®) or a combination of 1-hydroxycyclohexyl phenyl ketone and bis(2,6-dimethoxybenzoyl)-2,4-4-trimethylpentyl phosphine oxide (DMBAPO). In one embodiment a preferred method of polymerization initiation is visible light. In another bis(2,4,6-trimethylbenzoyl)-phenyl phosphine oxide (Irgacure 819®) is the photoinitiator.

The reaction mixture may also comprise at least one diluent or may be "neat". If a diluent is used, the selected diluents should solubilize the components in the reactive mixture. It will be appreciated that the properties of the selected hydrophilic and hydrophobic components may affect the properties of the diluents which will provide the desired compatibilization. For example, if the reaction mixture contains only moderately polar components, diluents having moderate δp may be used. If however, the reaction mixture contains strongly polar components, the diluent may need to have a high δp. However, as the diluent becomes more hydrophobic, processing steps necessary to replace the diluent with water will require the use of solvents other than water. This may undesirably increase the complexity and cost of the manufacturing process. Thus, it is important to select a diluent which provides the desired compatibility to the components with the necessary level of processing convenience.

The type and amount of diluent used also effects the properties of the resultant polymer and article. The haze, wettability and wettability of the final article may be improved by selecting relatively hydrophobic diluents and/or decreasing the concentration of diluent used.

Diluents useful in preparing the devices of this invention include ethers, esters, amides, alcohols, carboxylic acids and combinations thereof. Amides, carboxylic acids and alcohols are preferred diluents, and carboxylic acids, secondary and tertiary alcohols are more preferred diluents.

Examples of alcohols useful as diluents for this invention include those having the formula

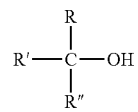

wherein R, R' and R" are independently selected from H, a linear, branched or cyclic monovalent alkyl having 1 to 10 carbons which may optionally be substituted with one or more groups including halogens, ethers, esters, aryls, amines, amides, alkenes, alkynes, carboxylic acids, alcohols, aldehydes, ketones or the like, or any two or all three of R, R' and R" can together bond to form one or more cyclic structures, such as alkyl having 1 to 10 carbons which may also be substituted as just described, with the proviso that no more than one of R, R' or R" is H.

It is preferred that R, R' and R" are independently selected from H or unsubstituted linear, branched or cyclic alkyl groups having 1 to 7 carbons. It is more preferred that R, R', and R" are independently selected form unsubstituted linear, branched or cyclic alkyl groups having 1 to 7 carbons. In certain embodiments, the preferred diluent has 4 or more, more preferably 5 or more total carbons, because the higher molecular weight diluents have lower volatility, and lower flammability. When one of the R, R' and R" is H, the structure forms a secondary alcohol. When none of the R, R' and R" are H, the structure forms a tertiary alcohol. Tertiary alcohols are more preferred than secondary alcohols. The diluents are preferably inert and easily displaceable by water when the total number of carbons is five or less.

Examples of useful secondary alcohols include 2-butanol, 2-propanol, menthol, cyclohexanol, cyclopentanol and exonorborneol, 2-pentanol, 3-pentanol, 2-hexanol, 3-hexanol, 3-methyl-2-butanol, 2-heptanol, 2-octanol, 2-nonanol, 2-decanol, 3-octanol, norborneol, and the like.

Examples of useful tertiary alcohols include tert-butanol, tert-amyl, alcohol, 2-methyl-2-pentanol, 2,3-dimethyl-2-butanol, 3-methyl-3-pentanol, 1-methylcyclohexanol, 2-methyl-2-hexanol, 3,7-dimethyl-3-octanol, 1-chloro-2-methyl-2-propanol, 2-methyl-2-heptanol, 2-methyl-2-octanol, 2-2-methyl-2-nonanol, 2-methyl-2-decanol, 3-methyl-3-hexanol, 3-methyl-3-heptanol, 4-methyl-4-heptanol, 3-methyl-3-octanol, 4-methyl-4-octanol, 3-methyl-3-nonanol, 4-methyl-4-nonanol, 3-methyl-3-octanol, 3-ethyl-3-hexanol, 3-methyl-3-heptanol, 4-ethyl-4-heptanol, 4-propyl-4-heptanol, 4-isopropyl-4-heptanol, 2,4-dimethyl-2-pentanol, 1-methylcyclopentanol, 1-ethylcyclopentanol, 1-ethylcyclopentanol, 3-hydroxy-3-methyl-1-butene, 4-hydroxy-4-methyl-1-cyclopentanol, 2-phenyl-2-propanol, 2 methoxy-2-methyl-2-propanol 2,3,4-trimethyl-3-pentanol, 3,7-dimethyl-3-octanol, 2-phenyl-2-butanol, 2-methyl-1-phenyl-2-propanol and 3-ethyl-3-pentanol, and the like.

Examples of useful carboxylic acids include $C_2$-$C_{16}$, carboxylic acids, with one or two carboxylic acid groups and optionally a phenyl group. Specific examples include acetic acid, decanoic acid, dodecanoic acid, octanoic acid, benzylic acid, thereof and the like.

A single alcohol or mixtures of two or more of the above-listed alcohols or two or more alcohols according to the structure above can be used as the diluent to make the polymer of this invention.

In certain embodiments, the diluent may be selected from secondary and tertiary alcohols having at least 4 carbons. Suitable examples of this embodiment include tert-butanol, tert-amyl alcohol, 2-butanol, 2-methyl-2-pentanol, 2,3-dimethyl-2-butanol, 3-methyl-3-pentanol, 3-ethyl-3-pentanol, 3,7-dimethyl-3-octanol.

In another embodiment the diluent may be selected from hexanol, heptanol, octanol, nonanol, decanol, tert-butyl alcohol, 3-methyl-3-pentanol, isopropanol, t amyl alcohol, ethyl lactate, methyl lactate, i-propyl lactate, 3,7-dimethyl-3-octanol, dimethyl formamide, dimethyl acetamide, dimethyl propionamide, N methyl pyrrolidinone and mixtures thereof. Additional diluents useful for this invention are disclosed in U.S. Pat. No. 6,020,445, and US 2010-0280146 A1 which is incorporated herein by reference.

In one embodiment of the present invention the diluent is water soluble at processing conditions and readily washed out of the lens with water in a short period of time. Suitable water soluble diluents include 1-ethoxy-2-propanol, 1-methyl-2-propanol, t-amyl alcohol, tripropylene glycol methyl ether, isopropanol, 1-methyl-2-pyrrolidone, N,N-dimethylpropionamide, ethyl lactate, dipropylene glycol methyl ether, mixtures thereof and the like. The use of a water soluble diluent allows the post molding process to be conducted using water only or aqueous solutions which comprise water as a substantial component.

The diluents may be used in amounts up to about 40% by weight of the total of all components in the reactive mixture. In one embodiment the diluent(s) are used in amounts less than about 30% and in another in amounts between about 2 and about 20% by weight of the total of all components in the reactive mixture.

It has been found that even amounts of diluent as low as 2-20 wt %, can lower the modulus of the resulting polymer by about 20% and improve wettability of the resulting polymers and lenses.

The diluent may also comprise additional components to lower the modulus of the resulting polymers and improve the lens curing efficiency and reducing residuals. Components capable of increasing the viscosity of the reactive mixture and/or increasing the degree of hydrogen bonding with the slow-reacting hydrophilic monomer, are desirable. Suitable components include polyamides, polylactams, such as PVP and copolymers thereof, polyols and polyol containing components such glycerin, boric acid, boric acid glycerol esters, polyalkylene glycols, combinations thereof and the like.

Suitable polylactams include PVP and copolymers comprising repeating units from NVP and hydrophilic monomers. In one embodiment, the polylactam is selected from, PVP, and the polyamide comprises DMA.

When polyamides or polylactams are used they have a molecular weight of between about K12-K120 (about 3900 to about 3,000,000 Dalton $M_w$) and in some embodiments from K30 to K90 (about 42,000 to about 1,300,000 Dalton $M_w$). Suitable polyalkylene glycols include polyethylene glycol and polypropylene glycols having molecular weight up to about 350 and in some embodiments less than about 200 gm/mol.

When used, the polyols, polyol containing components, polyamides and polylactams are used in amounts less than about 5 wt % or from about 0.2 to about 5 wt %. The diluents and co-diluents of the present invention also reduce the residuals remaining in the polymer at the end of the photocure. This provides lenses with more consistent properties, including diameter. In some embodiments the residual slow-reacting hydrophilic component present at the end of cure are less than about 2 wt % cured polymer ((wt of residual component/wt of cured polymer)*100%), or less than about 1 wt % and in some cases less than about 0.8 wt %. The reduction in residuals also leads to more consistent lens properties, including lens diameters, which can vary by less than about 0.05 mm.

The reactive mixture may contain additional components such as, but not limited to, medicinal agents, antimicrobial compounds, reactive tints, pigments, copolymerizable and non-polymerizable dyes, release agents and combinations thereof.

Combinations of reactive components and diluents include those having from about 20 to about 65 weight % silicone containing monomer, about 37 to about 70 weight % slow-reacting hydrophilic monomer, from about 2 to about 40 weight % of an hydroxyl containing component, from about 0.2 to about 3 weight % of at least one crosslinking monomer, from about 0 to about 3 weight % of a UV absorbing monomer, (all based upon the weight % of all reactive components). The mixture may further comprises between about 20 to about 60 weight % (weight % of all components, both reactive and non-reactive) of one or more diluents.

The reaction mixtures of the present invention can be formed by any of the methods known to those skilled in the art, such as shaking or stirring, and used to form polymeric articles or devices by known methods.

For example, the biomedical devices of the invention may be prepared by mixing reactive components and the diluent(s) with a polymerization initiator and curing by appropriate conditions to form a product that can be subsequently formed into the appropriate shape by lathing, cutting and the like. Alternatively, the reaction mixture may be placed in a mold and subsequently cured into the appropriate article.

Various processes are known for processing the reaction mixture in the production of contact lenses, including spincasting and static casting. Spincasting methods are disclosed in U.S. Pat. Nos. 3,408,429 and 3,660,545, and static casting methods are disclosed in U.S. Pat. Nos. 4,113,224 and 4,197,266. The method for producing contact lenses comprising the polymer of this invention may be by the direct molding of the silicone hydrogels, which is economical, and enables precise control over the final shape of the hydrated lens. For this method, the reaction mixture is placed in a mold having the shape of the final desired silicone hydrogel, i.e., water-swollen polymer, and the reaction mixture is subjected to conditions whereby the monomers polymerize, to thereby produce a polymer/diluent mixture in the shape of the final desired product.

Referring to FIG. 1, a diagram is illustrated of an ophthalmic lens 100, such as a contact lens, and mold parts 101-102 used to form the ophthalmic lens 100. In some embodiments, the mold parts include a back surface mold part 101 and a front surface mold part 102. As used herein, the term "front surface mold part" refers to the mold part whose concave surface 104 is a lens forming surface used to form the front surface of the ophthalmic lens. Similarly, the term "back surface mold part" refers to the mold part 101 whose convex surface 105 forms a lens forming surface, which will form the back surface of the ophthalmic lens 100. In some embodiments, mold parts 101 and 102 are of a concavo-convex shape, preferably including planar annular flanges, which surround the circumference of the uppermost edges of the concavo-convex regions of the mold parts 101-102.

Typically, the mold parts 101-102 are arrayed as a "sandwich". The front surface mold part 102 is on the bottom, with the concave surface 104 of the mold part facing upwards. The back surface mold part 101 can be disposed symmetrically on top of the front surface mold part 102, with the convex surface 105 of the back surface mold part 101 projecting partially into the concave region of the front surface mold part 102. The back surface mold part 101 may be dimensioned such that the convex surface 105 thereof engages the outer edge of the concave surface 104 of the front mold part 102 throughout its circumference, thereby cooperating to form a sealed mold cavity in which the ophthalmic lens 100 is formed.

The mold parts 101-102 may be fashioned of thermoplastic and are transparent to polymerization-initiating actinic radiation, by which is meant that at least some, and in some embodiments all, radiation of an intensity and wavelength effective to initiate polymerization of the reaction mixture in the mold cavity can pass through the mold parts 101-102.

For example, thermoplastics suitable for making the mold parts can include: polystyrene; polyvinylchloride; polyolefin, such as polyethylene and polypropylene; copolymers or mixtures of styrene with acrylonitrile or butadiene, polyacrylonitrile, polyamides, polyesters, cyclic olefin copolymers such as Topas available from Ticona or Zeonor available from Zeon, copolymers and blends of any of the foregoing, or other known material.

Following polymerization of the reaction mixture to form a lens 100, the lens surface 103 will typically adhere to the mold part surface 104. The steps of the present invention facilitate release of the surface 103 from the mold part surface. The first mold part 101 can be separated from the second mold part 102 in a demolding process. The lens 100 may have adhered to the second mold part 102 (i.e. the front curve mold part) during the cure process and remain with the second mold part 102 after separation until the lens 100 has been released from the front curve mold part 102. Alternatively, the lens 100 can adhere to the first mold part 101.

The lens 100 may be released from the mold by any process, including contacting with a solvent or dry release. For example, the lens 100 and the mold part to which it is adhered after demolding are contacted with an aqueous solution. The aqueous solution can be heated to any temperature below the boiling point of the aqueous solution. Heating can be accomplished with a heat exchange unit to minimize the possibility of explosion, or by any other feasible means or apparatus for heating a liquid.

As used herein, processing includes the steps of removing the lens from the mold and removing or exchanging the diluent with an aqueous solution. The steps may be done separately, or in a single step or stage. The processing temperature may be any temperatures between about 30° C. and the boiling point of the aqueous solutions, for example between about 30° C. and about 95° C., or between about 50° C. and about 95° C.

The aqueous solution is primarily water. In some embodiments, the aqueous solution is at least about 70 wt % water, and in other embodiments at least about 90 weight % water and in other embodiments at least about 95%. The aqueous solution may also be a contact lens packaging solution such as borate buffered saline solution, sodium borate solutions, sodium bicarbonate solutions and the like. The aqueous solution may also include additives, such as surfactants, preservatives, release aids, antibacterial agents, pharmaceutical and nutriceutical components, lubricants, wetting agents, salts, buffers, mixtures thereof and the like.

In one embodiment, devices made from the silicone hydrogels of the present invention further comprise at least one pharmaceutical and/or nutriceutical component. Pharmaceutical and nutriceutical components are known and include cationic drugs and neutriceuticals. Examples include those for the treatment of dry eye mitigation and/or prevention (including contact lens related dry eye, excessive tear evaporation and Non-Sjogren's aqueous tear deficiency), glaucoma, allergies (including antihistimines and mast cell inhibitors), ocular inflammation, ocular redness, ocular itching, bacterial, viral and fungal infections, prevention or slowing of myopia progression, and anaesthetics. Examples of cationic drugs include atropine, pirenzepine, doxycycline, brimonidine, brinzolamide, dorzolamide, betaxolol, apraclonidine, ccr2 antagonist, olopatadine, alcaftadine, betaxolol, bupivacaine, carbachol, carteolol, chlortetracycline, cyclopentolate, dibutoline, dipivefrin, ephedrine, erythromycin, gentamycin, gramicidin, homatropine ketotifen, levobunolol, levocabastine, lidocaine, lignocaine, lomefloxacin, mepivacaine, naphazoline, neomycin, ofloxacin, oxybuprocaine, pheniramine, physostigmine, pilocarpine, polymyxin B, proparacaine, pyrilamine, tetracaine, tetracycline, tetrahydrozoline, timolol, tropicamide, vidarabine, pharmaceutically acceptable salts thereof and combinations thereof and the like. In another embodiment suitable pharmaceutical components include atropine, pirenzepine, doxycycline, brimonidine, brinzolamide, dorzolamide, betaxolol, apraclonidine, ccr2 antagonist, olopatadine, alcaftadine, betaxolol, bupivacaine, carbachol, carteolol, chlortetracycline, cyclopentolate, dibutoline, dipivefrin, erythromycin, gentamycin, gramicidin, homatropine ketotifen, levobunolol, levocabastine, lidocaine, lignocaine, lomefloxacin, mepivacaine, naphazoline, ofloxacin, pheniramine, physostigmine, pilocarpine, polymyxin B, proparacaine, pyrilamine, tetracaine, tetrahydrozoline, timolol, tropicamide pharmaceutically acceptable salts thereof and combinations thereof and the like.

In another embodiment the cationic drugs include atropine, ketotifen, olopatadine, alcaftadine, levocabastine, pirenzepine, doxycycline, brimonidine, brinzolamide, dorzolamide, betaxolol, apraclonidine, ccr2 antagonist, olopatadine pharmaceutically acceptable salts thereof and combinations thereof and the like. The drugs may be incorporated into the lenses in a symptom mitigating effective amount. Suitable amounts will vary for each drug, but include those between about the weight of the drug contained in an ophthalmic device prior to its use by a patient wherein such minimum effective amount alleviates the symptoms of the condition being treated. The minimum effective amount may vary depending upon the efficacy of a particular drug. General ranges include between about 5 μg and about less than 200 μg, and in some embodiments between about 9 μg and about less than 100 μg, with the symptom mitigating effective amount being selected to achieve the desired clinical result while minimizing undesired side effects.

For example, if the anti-allergic agent is ketotifen fumarate, the minimum effective amount is between greater than about 9 μg and about less than 90 μg, more particularly between about 40 μg and greater than about 9 μg, most preferably about 20 μg.

In one embodiment, it is preferred that the minimum effective amount of drug alleviates the symptoms for between about 5 minutes, and about 24 hours from insertion of the ophthalmic device into the eye of a user, more preferably between about 5 minutes and about 16 hours, most preferably between about 5 minutes and about 12 hours.

The lenses of the present invention display surprisingly improved drug uptake compared to uncharged silicone hydrogel lenses and to anionic conventional lenses, such as etafilcon A. This is illustrated by the increase in uptake efficiency, uptake/[MAA], which was calculated using the following equation:

$$[(\text{Ketotifen uptake}_{ionic\ lens}/\text{Ketotifen uptake}_{non\text{-}ionic\ lens})/[\text{MAA}]_{ionic\ lens}] \times 100$$

Thus in one embodiment the lenses of the present invention display uptake efficiencies greater than about 200, greater than about 250, and in some embodiments, greater than about 300. While efficiency in the uptake of drug is increased, the uptake in polycationic ophthalmic solution component uptake, such as PQ1 uptake is maintained at a desirable level.

The ionic silicone hydrogel polymers of the present invention also display stable modulus. As used herein, stable modulus are those which increase less than about 30%, and in some embodiments less than about 20% over three autoclave cycles (20 minutes at 121° C.). In some embodiments the silicone hydrogel polymers of the present invention display modulus that increase by less than about 20% over 20 weeks over three autoclave cycles. In another embodiment, the ionic silicone hydrogels of the present invention display modulii which change less than about 30%, about 20% or even less than about 10% over 12 or 18 months at 25° C. and ambient humidity.

Still further the invention includes a method of making an ophthalmic device comprising about a minimum effective amount of an anti-allergic agent comprising the step of treating an ophthalmic device with a solution comprising said anti-allergic agent, wherein the amount of said anti-allergic agent in said solution exceeds the minimum effective amount.

It is preferred that the minimum effective amount is exceeded by between about 1.0% and about 1000%, in a volume of solution that is between about 500 μL and about 5000 μL preferably between about 50% and about 500%, in a volume of solution that is between about 500 μL and about 3000 μL most preferably about 50% in a volume of solution that is about 1000 μL.

As used herein treating means physical methods of contacting the solution containing an anti-allergic agent and the ophthalmic device. Preferably treating refers to physical methods of contacting the anti-allergic agent with the ophthalmic devices prior to selling or otherwise delivering the ophthalmic devices to a patient. The ophthalmic devices may be treated with the anti-allergic agent anytime after they are polymerized.

Additional examples of additives which may be included in the aqueous solution include Tween® 80, which is polyoxyethylene sorbitan monooleate, Tyloxapol, octylphenoxy (oxyethylene) ethanol, amphoteric 10), EDTA, sorbic acid, DYMED, chlorhexadine gluconate, hydrogen peroxide, thimerosal, polyquad, polyhexamethylene biguanide, mixtures thereof and the like. Where various zones are used, different additives may be included in different zones. Additives may be added to the hydration solution in amounts varying between 0.01% and 10% by weight, but cumulatively less than about 10% by weight.

Exposure of the ophthalmic lens 100 to the aqueous solution can be accomplished by any method, such as washing, spraying, soaking, submerging, or any combination of the aforementioned. For example, the lens 100 can be washed with an aqueous solution comprising deionized water in a hydration tower.

Using a hydration tower, front curve mold parts 102 containing lenses 100 can be placed in pallets or trays and stacked vertically. The aqueous solution can be introduced at the top of the stack of lenses 100 so that the solution will flow downwardly over the lenses 100. The solution can also be introduced at various positions along the tower. The trays can be moved upwardly allowing the lenses 100 to be exposed to increasingly fresher solution.

Alternatively, the ophthalmic lenses 100 may be soaked or submerged in the aqueous solution.

The contacting step can last up to about 12 hours, in some embodiments up to about 2 hours and in other embodiments from about 2 minutes to about 2 hours; however, the length of the contacting step depends upon the lens materials, including any additives, the materials that are used for the solutions or solvents, and the temperatures of the solutions. Sufficient treatment times typically shrink the contact lens and release the lens from the mold part. Longer contacting times will provide greater leaching.

The volume of aqueous solution used may be any amount greater than about 1 ml/lens and in some embodiments greater than about 5 ml/lens.

In some methods, after separation or demolding, the lenses on the front curves, which may be part of a frame, are mated with individual concave slotted cups to receive the contact lenses when they release from the front curves. The cups can be part of a tray. Examples can include trays with 32 lenses each, and 20 trays that can be accumulated into a magazine.

Alternatively, the lenses may be submerged in the aqueous solution. Magazines can be accumulated and then lowered into tanks containing the aqueous solution. The aqueous solution may also include other additives as described above.

The ophthalmic devices, and particularly ophthalmic lenses of the present invention, have a balance of properties which makes them particularly useful. Such properties include clarity, optics, water content, oxygen permeability and advancing contact angle. Thus, the biomedical devices may be contact lenses having a water content of greater than about 55%, greater than about 60%.

As used herein clarity means substantially free from visible haze. Clear lenses have a haze value of less than about 70%, more preferably less than about 50% or less than about 10%.

Suitable oxygen permeabilities include those greater than about 80 barrers, greater than about 85 barrer, or at least about 100 barrer.

Also, the biomedical devices, and particularly ophthalmic devices and contact lenses have moduli which are less than about 150 psi, or less than about 100 psi.

The biomedical devices, and particularly ophthalmic devices and contact lenses have average contact angles (advancing) which are less than about 80°, less than about 75° or less than about 70°. The articles of the present invention may have combinations of the above described oxygen permeability, water content and contact angle. All combinations of the above ranges are deemed to be within the present invention.

Human tears are complex and contain a mixture of proteins, lipids and other components which help to keep the eye lubricated. Examples of lipids classes include wax ester, cholesterolesters and cholesterol. Examples of proteins which are found in human tears include lactoferrin, lysozyme, lipocalin, serum albumin, secretory immunoglobulin A.

Lysozyme is generally present in human tears in substantial concentrations. Lysozyme is bacteriolytic and believed to protect the eye against bacterial infection. The amount of lysozyme which associates with commercially available contact lenses varies greatly from only a few micrograms to over 800 micrograms for etafilcon A contact lenses (commercially available from Johnson & Johnson Vision Care, Inc., under the ACUVUE and ACUVUE2 brand names). Etafilcon A contact lenses have been commercially available for many years and display some of the lowest adverse event rates of any soft contact lens. Thus, contact lenses which uptake substantial levels of lysozyme are desirable. The lenses of the present invention uptake at least about 30 µg, 50 µg, 100 µg, of lysozyme, all from a 2 mg/ml solution over 72 hours incubation at 35° C.

The form of the proteins in, on and associated with the lens is also important. Denatured proteins are believed to contribute to corneal inflammatory events and wearer discomfort. Environmental factors such as pH, ocular surface temperature, wear time and closed eye wear are believed to contribute to the denaturation of proteins. However, lenses of different compositions can display markedly different protein uptake and denaturation profiles. In one embodiment of the present invention, a majority of the proteins uptaken by the lenses of the present invention are and remain in the native form during wear. In other embodiments at least about 50%, at least about 70 and at least about 80% of uptaken proteins are and remain native after 24 hours, 3 days and during the intended wear period.

In one embodiment the ophthalmic devices of the present invention also uptake less than about 20%, in some embodiments less than about 10%, and in other embodiments less than about 5% Polyquaternium-1 (dimethyl-bis[(E)-4-[tris (2-hydroxyethyl)azaniumyl]but-2-enyl]azanium trichloride) ("PQ1") from an ophthalmic solution containing 0.001 wt % PQ1).

Hansen Solubility Parameter

The Hansen solubility parameter, δp may be calculated by using the group contribution method described in Barton, CRC Handbook of Solubility Par., 1st. Ed. 1983, page 85-87 and using Tables 13, 14.

Haze Measurement

Haze is measured by placing a hydrated test lens in borate buffered saline in a clear 20×40×10 mm glass cell at ambient temperature above a flat black background, illuminating from below with a fiber optic lamp (Dolan-Jenner PL-900 fiber optic light or Titan Tool Supply Co. fiber optic light with 0.5" diameter light guide set at a power setting of 4-5.4) at an angle 66° normal to the lens cell, and capturing an image of the lens from above, normal to the lens cell with a video camera (DVC 1300C:19130 RGB camera with Navitar TV Zoom 7000 zoom lens) placed 14 mm above the lens platform. The background scatter is subtracted from the scatter of the lens by subtracting an image of a blank cell using EPIX XCAP V 2.2 software. The subtracted scattered light image is quantitatively analyzed, by integrating over the central 10 mm of the lens, and then comparing to a −1.00 diopter CSI Thin Lens®, which is arbitrarily set at a haze value of 100, with no lens set as a haze value of 0. Five lenses are analyzed and the results are averaged to generate a haze value as a percentage of the standard CSI lens.

Alternatively, instead of a −1.00 diopter CSI Thin Lenses®, a series of aqueous dispersions of stock latex spheres (commercially available as 0.49 µm Polystyene Latex Spheres—Certified Nanosphere Size Standards from Ted Pella, Inc., Product Number 610-30) can be used as standards. A series of calibration samples were prepared in deionized water. Each solution of varying concentration was placed in a cuvette (2 mm path length) and the solution haze was measured using the above method.

| Solution | Concentration (wt % ×10$^{-4}$) | Mean GS |
|---|---|---|
| 1 | 10.0 | 533 |
| 2 | 6.9 | 439 |
| 3 | 5.0 | 379 |
| 4 | 4.0 | 229 |
| 5 | 2.0 | 172 |
| 6 | 0.7 | 138 |

Mean GS = mean gray scale

A corrective factor was derived by dividing the slope of the plot of Mean GS against the concentration (47.1) by the slope of an experimentally obtained standard curve, and multiplying this ratio times measured scatter values for lenses to obtain GS values.

"CSI haze value" may be calculated as follows:

CSI haze value=100×(GS−BS)/(217−BS)

Where GS is gray scale and BS is background scatter.

Water Content

The water content of contact lenses was measured as follows: Three sets of three lenses are allowed to sit in packing solution for 24 hours. Each lens is blotted with damp wipes and weighed. The lenses are dried at 60° C. for four hours at a pressure of 0.4 inches Hg or less. The dried lenses are weighed. The water content is calculated as follows:

$$\% \text{ water content} = \frac{(\text{wet weight} - \text{dry weight})}{\text{wet weight}} \times 100$$

The average and standard deviation of the water content are calculated for the samples and are reported.

Modulus

Modulus is measured by using the crosshead of a constant rate of movement type tensile testing machine equipped with a load cell that is lowered to the initial gauge height. A suitable testing machine includes an Instron model 1122. A dog-bone shaped sample having a 0.522 inch length, 0.276 inch "ear" width and 0.213 inch "neck" width is loaded into the grips and elongated at a constant rate of strain of 2 in/min. until it breaks. The initial gauge length of the sample (Lo) and sample length at break (Lf) are measured. Twelve specimens of each composition are measured and the average is reported. Percent elongation is =[(Lf−Lo)/Lo]×100. Tensile modulus is measured at the initial linear portion of the stress/strain curve.

Advancing Contact Angle

All contact angles reported herein are advancing contact angles. The advancing contact angle was measured as follows. Four samples from each set were prepared by cutting out a center strip from the lens approximately 5 mm in width and equilibrated in packing solution. The wetting force between the lens surface and borate buffered saline is measured at 23° C. using a Wilhelmy microbalance while the sample is being immersed into or pulled out of the saline. The following equation is used $$F = 2\gamma p \cos\theta \text{ or } \theta = \cos^{-1}(F/2\gamma p)$$

where F is the wetting force, $\gamma$ is the surface tension of the probe liquid, p is the perimeter of the sample at the meniscus and $\theta$ is the contact angle. The advancing contact angle is obtained from the portion of the wetting experiment where the sample is being immersed into the packing solution. Each sample was cycled four times and the results were averaged to obtain the advancing contact angles for the lens.

Oxygen Permeability (Dk)

The Dk is measured as follows. Lenses are positioned on a polarographic oxygen sensor consisting of a 4 mm diameter gold cathode and a silver ring anode then covered on the upper side with a mesh support. The lens is exposed to an atmosphere of humidified 2.1% $O_2$. The oxygen that diffuses through the lens is measured by the sensor. Lenses are either stacked on top of each other to increase the thickness or a thicker lens is used. The L/Dk of 4 samples with significantly different thickness values are measured and plotted against the thickness. The inverse of the regressed slope is the Dk of the sample. The reference values are those measured on commercially available contact lenses using this method. Balafilcon A lenses available from Bausch & Lomb give a measurement of approx. 79 barrer. Etafilcon lenses give a measurement of 20 to 25 barrer. (1 barrer=$10^{-10}$ ($cm^3$ of gas×$cm^2$)/($cm^3$ of polymer×sec×cm Hg)).

Lysozyme, Lipocalin & Mucin Uptake

Lysozyme uptake was measured as follows: The lysozyme solution used for the lysozyme uptake testing contained lysozyme from chicken egg white (Sigma, L7651) solubilized at a concentration of 2 mg/ml in phosphate saline buffer supplemented by Sodium bicarbonate at 1.37 g/l and D-Glucose at 0.1 g/l.

Three lenses for each example were tested using each protein solution, and three were tested using PBS (phosphate buffered saline) as a control solution. The test lenses were blotted on sterile gauze to remove packing solution and aseptically transferred, using sterile forceps, into sterile, 24 well cell culture plates (one lens per well) each well containing 2 ml of lysozyme solution. Each lens was fully immersed in the solution. 2 ml of the lysozyme solution was placed in a well without a contact lens as a control.

The plates containing the lenses and the control plates containing only protein solution and the lenses in the PBS, were parafilmed to prevent evaporation and dehydration, placed onto an orbital shaker and incubated at 35° C., with agitation at 100 rpm for 72 hours. After the 72 hour incubation period the lenses were rinsed 3 to 5 times by dipping lenses into three (3) separate vials containing approximately 200 ml volume of PBS. The lenses were blotted on a paper towel to remove excess PBS solution and transferred into sterile conical tubes (1 lens per tube), each tube containing a volume of PBS determined based upon an estimate of lysozyme uptake expected based upon on each lens composition. The lysozyme concentration in each tube to be tested needs to be within the albumin standards range as described by the manufacturer (0.05 micogram to 30 micrograms). Samples known to uptake a level of lysozyme lower than 100 μg per lens were diluted 5 times. Samples known to uptake levels of lysozyme higher than 500 μg per lens (such as etafilcon A lenses) are diluted 20 times.

1 ml aliquot of PBS was used for all samples other than etafilcon. 20 ml were used for etafilcon A lens. Each control lens was identically processed, except that the well plates contained PBS instead of lysozyme solution.

Lysozyme uptake was determined using on-lens bicinchoninic acid method using QP-BCA kit (Sigma, QP-BCA) following the procedure described by the manufacturer (the standards prep is described in the kit) and is calculated by subtracting the optical density measured on PBS soaked lenses (background) from the optical density determined on lenses soaked in lysozyme solution.

Optical density was measured using a SynergyII Microplate reader capable for reading optical density at 562 nm.

Lipocalin uptake was measured using the following solution and method. The lipocalin solution contained B Lactoglobulin (Lipocalin) from bovine milk (Sigma, L3908) solubilized at a concentration of 2 mg/ml in phosphate saline buffer (Sigma, D8662) supplemented by sodium bicarbonate at 1.37 g/l and D-Glucose at 0.1 g/l.

Three lenses for each example were tested using the lipocalin solution, and three were tested using PBS as a control solution. The test lenses were blotted on sterile gauze to remove packing solution and aseptically transferred, using sterile forceps, into sterile, 24 well cell culture plates (one lens per well) each well containing 2 ml of lipocalin solution. Each lens was fully immersed in the solution. Control lenses were prepared using PBS as soak solution instead of lipocalin. The plates containing the lenses immersed in lipocalin solution as well as plates containing control lenses immersed in PBS, were parafilmed to prevent evaporation and dehydration, placed onto an orbital shaker and incubated at 35° C., with agitation at 100 rpm for 72 hours. After the 72 hour incubation period the lenses were rinsed 3 to 5 times by dipping lenses into three (3) separate vials containing approximately 200 ml volume of PBS. The lenses were blotted on a paper towel to remove excess PBS solution and transferred into sterile 24 well plates each well containing 1 ml of PBS solution.

Lipocalin uptake was determined using on-lens bicinchoninic acid method using QP-BCA kit (Sigma, QP-BCA) following the procedure described by the manufacturer (the standards prep is described in the kit) and is calculated by subtracting the optical density measured on PBS soaked lenses (background) from the optical density determined on lenses soaked in lipocalin solution. Optical density was measured using a SynergyII Micro-plate reader capable for reading optical density at 562 nm.

Mucin uptake was measured using the following solution and method. The Mucin solution contained Mucins from bovine submaxillary glands (Sigma, M3895-type 1-S) solubilized at a concentration of 2 mg/ml in phosphate saline buffer (Sigma, D8662) supplemented by sodium bicarbonate at 1.37 g/l and D-Glucose at 0.1 g/l.

Three lenses for each example were tested using Mucin solution, and three were tested using PBS as a control solution. The test lenses were blotted on sterile gauze to remove packing solution and aseptically transferred, using sterile forceps, into sterile, 24 well cell culture plates (one lens per well) each well containing 2 ml of Mucin solution. Each lens was fully immersed in the solution. Control lenses were prepared using PBS as soak solution instead of lipocalin.

The plates containing the lenses immersed in Mucin as well as plates containing control lenses immersed in PBS were parafilmed to prevent evaporation and dehydration, placed onto an orbital shaker and incubated at 35° C., with agitation at 100 rpm for 72 hours. After the 72 hour incubation period the lenses were rinsed 3 to 5 times by dipping lenses into three (3) separate vials containing approximately 200 ml volume of PBS. The lenses were blotted on a paper towel to remove excess PBS solution and transferred into sterile 24 well plates each well containing 1 ml of PBS solution.

Mucin uptake was determined using on-lens bicinchoninic acid method using QP-BCA kit (Sigma, QP-BCA) following the procedure described by the manufacturer (the standards prep is described in the kit) and is calculated by subtracting the optical density measured on PBS soaked lenses (background) from the optical density determined on lenses soaked in Mucin solution. Optical density was measured using a SynergyII Micro-plate reader capable for reading optical density at 562 nm.

Kinetics
Preparation of Reactive Monomer Mixes: 15-20 g Batch

The preparation of the reactive monomer mixtures for the kinetics studies were prepared under yellow light as follows. The components for each kinetics example were weighed into a 20 mL amber borosilicate glass scintillation vial (Wheaton 320 brand; Catalogue #80076-576, or equivalent). Vials were capped (using PTFE lined green cap, Qorpak; Supplier #5205/100, Catalogue #16161-213) and rolled on jar roller until all solids were dissolved and a homogeneous mixtures were obtained.

Degas

Figure 2:
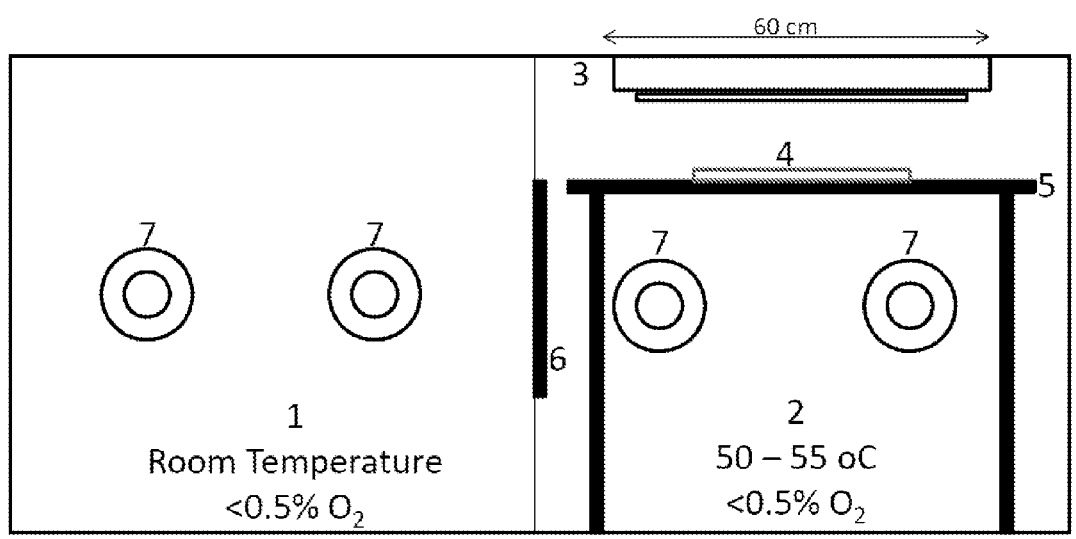
FIG. 2 is a schematic of the dual compartment cure box used for the kinetic evaluations.

Reactive monomer mixes were degassed under vacuum, under yellow light for 7-10 minutes, and back-filling with nitrogen after breaking vacuum. Vials were quickly capped and placed in compartment 1 of a two compartment nitrogen cure box, via the gated aperature, 7, as shown in FIG. 2. The conditions in compartment 1 were room temperature and <0.5% oxygen (using continuous nitrogen purge).

Nitrogen Cure Box—Compartment 2

The oxygen level in both compartments was maintained by continuous/constant nitrogen purge. The temperature in Compartment 2 was maintained by a heater (COY, Laboratory Products Inc.). The nitrogen cure box was allowed to equilibrate for a minimum of 4 hours prior to performing each kinetics study. The degassed reactive mixture (in tightly capped amber vial) was placed in compartment 1 during the equilibration period.

Light Source and Intensity Setting

Figure 3:
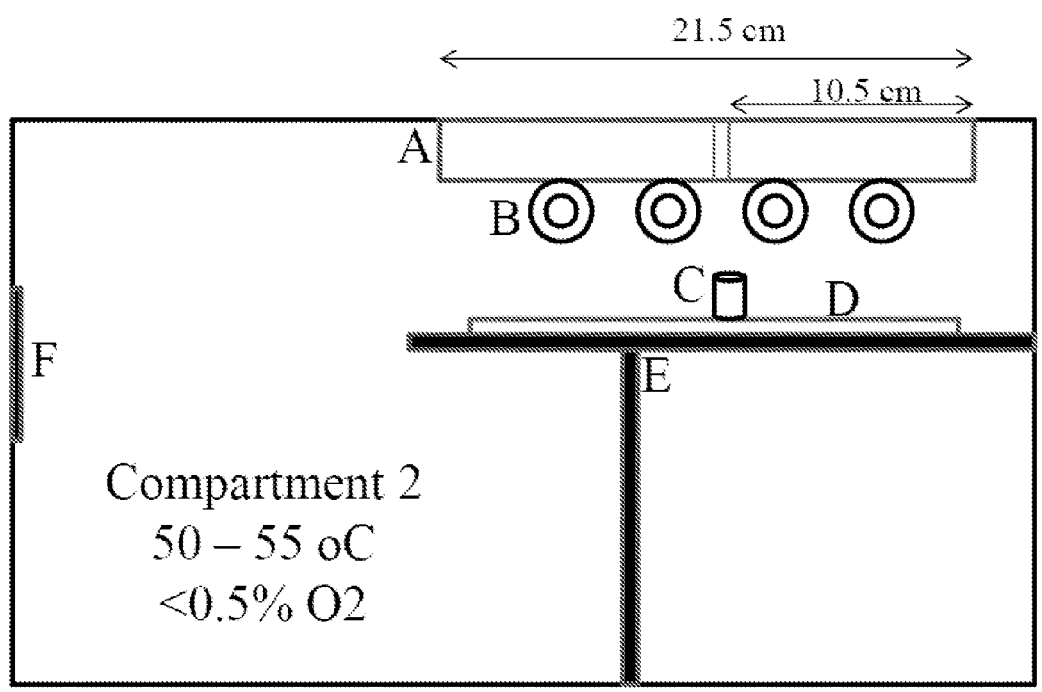
FIG. 3 is a schematic of compartment 2 of the cure box show in FIG. 2

As depicted in FIG. 3, 2 fluorescent light fixtures (Lithonia Lighting Fluorescent Luminaire (Gas Tube Luminaire), 60 cm×10.5 cm) each equipped with 2 fluorescent lamps (Philips TLK 40 W/03, 58 cm) were arranged in parallel. The cure intensity was attenuated by adjusting the height of the shelf (shown in FIGS. 2 and 3) relative to the light source. The intensity at a given shelf height was measured by placing the sensor of a calibrated radiometer/photometer on the mirrored surface, consistent with the position of the sample, as shown in FIG. 3. The sensor was placed directly under the space between the $2^{nd}$ and $3^{rd}$ lamps in the 4 lamps arrangement.

Using a calibrated analytical balance (4 decimal places) the weight of a clear borosilicate glass scintillation vial (Wheaton 986541) with cap (white cap with polyethylene insert) was determined The vial with cap was transferred to Compartment 1 of the Nitrogen Cure Box. The cap was unscrewed and using a calibrated 10-100 µL Eppendorf Pipet, 100 µL of the Reactive Monomer Mixture was transferred into the vial. The vial was tightly capped, quickly moved into Compartment 2, via door 6, and placed on the mirrored surface 4, as shown in FIG. 2. The sample was placed directly under the space between the $2^{nd}$ and $3^{rd}$ lamps in the 4 lamps arrangement. The light source 3, was turned on and the sample was exposed for a specified time period. Although the light source was set at 4-5 mW/cm², the actual intensity reaching the sample is 0.7-1.3 mW/cm², due the cap on the sample glass vials. After exposure, the light source 3, was turned off and the vial (with cap) was re-weighed to determine the sample weight by difference. Using a calibrated 500-5000 µL Eppendorf Pipet, 10 mL HPLC grade methanol was added to the vial.

Aliquots (100 µL) of the Reactive Monomer Mixture were pipetted into separate borosilicate glass scintillation vials and the above procedure described above was performed to generate samples at the following minimum time points (minutes): 0, 0.25, 0.50, 0.75, 1, 2, 4, 6, 8, 10.

Cured polymers were extracted in methanol overnight by gently shaking at room temperature.

Extracts were analyzed for residual components by High Performance Liquid Chromatography with UV detection (HPLC/UV) using the following procedures.

Quantitation of the mPDMS in the extracts was performed against external calibration standards (about 6-11, using the response of the n=6 oligomer), typically covering the range of 1 µg/mL-800 µg/mL. If the concentrations of mPDMS in the extracts were outside the calibration range, the extracts were diluted with methanol to render concentrations within the calibration range for more accurate quantitation.

Chromatographic Conditions
Column: Agilent Zorbax Eclipse XDB18, 4.6×50 mm×1.8 µm
Column Temperature: 30° C.
UV Detector: 217 nm
Injection Volume: 20 µL
Mobile Phase
Eluent A: De-ionized
Eluent B: Acetonitrile
Eluent C: Isopropanol
Flow Rate: 1 mL/min

| Time (mins) | % A | % B | % C |
|---|---|---|---|
| 0.0 | 50 | 48 | 2 |
| 0.5 | 50 | 48 | 2 |
| 2.0 | 0 | 60 | 40 |
| 5.0 | 0 | 60 | 40 |
| 5.1 | 0 | 30 | 70 |
| 8.0 | 0 | 30 | 70 |
| 8.1 | 50 | 48 | 2 |
| 10.0 | 50 | 48 | 2 |

Quantitation of the components in the extracts other than mPDMS was performed against external calibration standards (about 6-11) for each component, typically covering the range of 1 µg/mL-800 µg/mL. If the concentrations of components in the extracts were outside the calibration range, the extracts were appropriately diluted with methanol to render concentrations within the calibration range for more accurate quantitation.

Chromatographic Conditions
Column: Agilent Zorbax Eclipse Plus 18, 4.6×75 mm×1.8 μm
Column Temperature: 30° C.
UV Detector: 217 nm
Injection Volume: 5 μL
Mobile Phase
Eluent A: De-ionized water with 0.05% $H_3PO_4$
Eluent B: Acetonitrile with 0.05% $H_3PO_4$
Eluent C: Methanol
Flow Rate: 1 mL/min

| Time (mins) | % A | % B | % C |
|---|---|---|---|
| 0 | 95 | 5 | 0 |
| 5 | 95 | 5 | 0 |
| 15 | 0 | 100 | 0 |
| 23 | 0 | 100 | 0 |
| 24 | 0 | 30 | 70 |
| 28 | 0 | 30 | 70 |
| 29 | 95 | 5 | 0 |
| 35 | 95 | 5 | 0 |

Calculations
1. At each time point the following values are determined:
The concentration (μg/mL) of each component in the sample extract.
The concentration of each component in the sample extract, expressed as a percent of the sample weight as follows:

% Component=[(μg/mL*Volume of Extract*Dilution Factor*$10^{-6}$ g/μg)/(g Sample Weight)]*100

The percent unreacted component present, expressed as a percent relative to $T_0$ (where $T_0$ represented 100% unreacted component)

% at $T_x$=(% Measured at $T_x$/% Measured at $T_0$)*100

2. Using the % Component calculated above, the concentration of each component in μmoles/g, is calculated as follows:

μmoles/g=(% Component*$10^3$)/(Molecular Weight of Component)

3. Using the concentration of each component determined in μmoles/g in step 2, the concentration at $Time_x$ was expressed as Log $[A_x]/[A_o]$, where $[A_x]$ is the concentration of component A at x minutes and $[A_o]$ is the concentration of component A at 0 minutes ($T_o$)
The expression Log $[A_x]/[A_o]$ was determined for each time point.
First order kinetics were assumed for determining both the polymerization kinetics rate and half life for each component. The following equations were used for calculating polymerization rate Log $[A_t]/[A_0]$=−kt/2.303 and half life ln $[A_0]/[0.5A_0]$=$kt_{1/2}$ or $t_{1/2}$=0.693/k

For each component, a plot of Log $[A_x]/[A_0]$ versus time (minutes) was generated. Typically, the data points (x, y) that best correspond to linear growth (shorter cure times) were plotted and the data were fitted to a linear equation.
Using the slope, the kinetic rate constant (k) of each component was evaluated from the following equation:

k(minute$^{-1}$)=Slope*−2.303

The half-life (minutes) of each component was evaluated from the following equation:

$t_{1/2}$=0.693/k

The evaluated half-life for each component was compared to the data generated for the percent of each component relative to $T_o$, at each time point. Typically for each component, the time taken to attain 50% consumption was close to the half-life based on $1^{st}$ order kinetics. In cases where the two were significantly different (typically about 30% for half-life of less than about 1 minute, 25% for half-life less than about 2.5 minutes but greater than 1 minute and 20% for half-life greater than 2.5 minutes), the data points (x, y) were re-evaluated to generate kinetic rate constants (k) which would provide half-lives (based on $1^{st}$ order considerations) more consistent (within 20%) with the measured values.

The Examples below further describe this invention, but do not limit the invention. They are meant only to suggest a method of practicing the invention. Those knowledgeable in the field of contact lenses as well as other specialties may find other methods of practicing the invention. However, those methods are deemed to be within the scope of this invention. Some of the other materials that are employed in the Examples are identified as follows:

EXAMPLES

The following abbreviations are used in the examples below:
FC Front mold curves
BC Back mold curves
SiMAA (3-methacryloxy-2-hydroxypropoxy)propyl-bis(trimethylsiloxy)methylsilane (Also known as SiGMA)
DMA N,N-dimethylacrylamide
HEMA 2-hydroxyethyl methacrylate
HEAA hydroxyethylacrylamide
HBMA 2-hydroxybutyl methacrylate, prepared as in Example XX
HPMA 2-hydroxypropyl methacrylate (ACROS)
DMHEMA dimethylhydroxyethylmethacrylate, prepared as in Example XY
mPDMS 800-1000 MW ($M_n$) monomethacryloxypropyl terminated mono-n-butyl terminated polydimethylsiloxane
OH-mPDMS α-(2-hydroxy-1-methacryloxypropyloxypropyl)-ω-butyl-decamethylpentasiloxane, (MW 612 g/mol), prepared as in Example 8 of US20100249356 A1
Norbloc 2-(2'-hydroxy-5-methacrylyloxyethylphenyl)-2H-benzotriazole
D3O 3,7-dimethyl-3-octanol
IPA isopropyl alcohol
TAC triallylcyanurate
TEGDMA tetraethyleneglycol dimethacrylate
TRIS 3-methacryloxypropyltris(trimethylsiloxy)silane
CGI 819 bis(2,4,6-trimethylbenzoyl)-phenylphosphineoxide
EtOAc ethyl acetate
DA decanoic acid
GMMA 2,3-dihydroxypropyl methacrylate
TAA t-amyl alcohol
ETOH ethanol
SA-2 N-(2,3-dihydroxypropane)-N'-(propyl tetra(dimethylsiloxy)dimethylbutylsilane)acrylamide, as shown in Formula XI

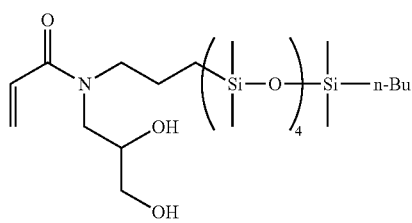

VMA N-vinyl-N-methyl acetamide
NVP N-vinylpyrrolidone
BHT butylated hydroxytoluene
PVP poly(N-vinylpyrrolidone)
VINAL an ionic amide containing vinyl ether having the structure

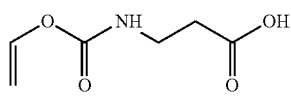

and prepared in Synthetic Preparation 3
BAE (Boric Acid Ester) was formed as follows:

1.24 parts of a 5% (wt) solution of ethylenediaminetetraacetic acid, 299 parts (wt) glycerol and 100 parts (wt) boric acid were added to a reaction flask. The mixture was heated with stirring to 90° C. Vacuum was applied to reduce the pressure to less than 6 torr as the mixture was stirred for 155 minutes, with removal of water vapor. The pressure was reduced to less than 2 torr and the reaction was continued for 2 hours, or longer as needed until the % water of the mixture was reduced to less than 0.2% using a Karl Fischer test.

BAGE (Boric Acid Glycerol Ester) was formed as follows:

To BAE prepared as described above was added 624 parts (wt) glycerol with stirring for 60 minutes at 35-40° C.

Example 1 and Comparative Example 1

A reaction mixture was formed by mixing the components listed in Table 1 and degassed by applying vacuum at ambient temperature for about 17(±3) minutes. The reaction mixture (75 μL) was then dosed at room temperature and <0.5% $O_2$, into thermoplastic contact lens molds (FC—Zeonor, BC Polypropylene) which had been degassed in $N_2$ box at RT (Compartment 1, FIG. 1) for a minimum of 12 hours prior to dosing. The BC was placed on the FC mold to produce 8 BC/FC assemblies in a pallet. Eight pallets were assembled and moved into the cure compartment (Compartment 2, FIG. 1). Pallets were placed on a mirrored surface and a quartz plate (0.50 mm thick) was placed over each pallet. The lenses were cured for 18 minutes, at an intensity of 4-5 mW/cm², <0.5% $O_2$, and 50-55° C.

The molds were manually demolded (lenses remained in FC) and lenses were released in 50/50 IPA/$H_2O$ (8 pallets, 8 lenses per pallet), 1 L solution, 1 hour.

Lenses were "stepped down" into PS in the following order: 25/75IPA/$H_2O$ (10 mins), $H_2O$ (30 mins), $H_2O$ (10 mins), $H_2O$ (10 mins), and stored in borate buffered packing solution in lens vials and sterilized at 122° C. for 30 minutes.

TABLE 1

| Component | Ex. 1 NVP | CE 1 DMA |
|---|---|---|
| OH-mPDMS, n = 4 | 40 | 40 |
| NVP | 50.5 | 0 |
| DMA | 0 | 50.5 |
| HEMA | 6.75 | 6.75 |
| TEGDMA | 0.5 | 0.5 |
| Norblock | 2 | 2 |
| CGI 819 | 0.25 | 0.25 |

TABLE 2

| Ex. # | % $H_2O$ | % Haze | DCA | Mechanicals | | Dk |
| | | | | Mod. (psi) | Elong. (%) | |
|---|---|---|---|---|---|---|
| 1 | 58.4 (0.2) | 4 (0) | 44 (4) | 102.9 (11.4) | 220.3 (36.2) | 74.7 |
| CE1 | 59.8 (0.1) | 5 (1) | 127 (14) | 54.1 (7.4) | 227.3 (52.3) | 48.5 |

The lenses of Example 1 exhibited exceptional haze (4%), wettability (DCA) 44°, modulus, elongation and Dk. The lenses of Comparative Example 1 exhibited greatly increased contact angle (127°), indicating a marked decrease in wettability. Comparative Example 1 also displayed a substantially reduced modulus (54.1 psi) and oxygen permeability (48.5) compared to Example 1 (102.9 and 74.7, respectively).

Examples 2 and Comparative Example 2

The polymerization rate and half life for each component in the Formulations of Example 1 and Comparative Example 1 were determined using the procedure described in the kinetics section above. In each Example, for each of the components in the sample extract and at each of the time points the following information is reported, the wt % of each residual component measured (Table 3), % incorporation of each residual component at each time point relative to the % residual measured at $T_o$ (Table 4), the μmole/g of each residual component at each time point (Table 5) and, log $[A]/[A_o]$ (Table 6), and the polymerization rate constants and half-lives (Tables 7 and 8).

TABLE 3

| Cure Time | Ex. 2 RESIDUAL MONOMERS WT % | | | | | |
| | NVP | HEMA | TEGDMA | Norbloc | CGI 819 | OH-mPDMS |
|---|---|---|---|---|---|---|
| 0.00 | 48.687 | 6.612 | 0.493 | 2.036 | 0.211 | 36.999 |
| 0.25 | 50.127 | 5.740 | 0.377 | 1.805 | 0.167 | 33.584 |
| 0.50 | 50.053 | 4.958 | 0.303 | 1.602 | 0.129 | 29.903 |
| 1.00 | 48.037 | 3.611 | 0.185 | 1.152 | 0.067 | 22.854 |
| 2.00 | 45.327 | 1.722 | 0.072 | 0.554 | 0.020 | 11.709 |
| 4.00 | 37.315 | 0.520 | 0.030 | 0.085 | 0.002 | 3.724 |
| 6.00 | 34.959 | 0.439 | 0.027 | 0.037 | | 3.393 |
| 8.00 | 32.155 | 0.330 | 0.021 | 0.016 | | 2.562 |
| 10.00 | 24.624 | | | | | |
| 12.00 | 21.977 | | | | | |
| 15.00 | 17.041 | | | | | |
| 20.00 | 8.579 | | | | | |
| 30.00 | 3.241 | | | | | |

TABLE 4

Ex. 2% Incorporation

| Cure Time | % NVP | % HEMA | % TEGDMA | % Norbloc | % CGI 819 | % OH-mPDMS |
|---|---|---|---|---|---|---|
| 0.00 | 100.00 | 100.00 | 100.00 | 100.00 | 100.00 | 100.00 |
| 0.25 | 102.96 | 86.81 | 76.49 | 88.65 | 79.13 | 90.77 |
| 0.50 | 102.81 | 74.99 | 61.35 | 78.69 | 61.15 | 80.82 |
| 1.00 | 98.67 | 54.61 | 37.56 | 56.59 | 31.64 | 61.77 |
| 2.00 | 93.10 | 26.04 | 14.55 | 27.19 | 9.44 | 31.65 |
| 4.00 | 76.64 | 7.86 | 6.10 | 4.18 | 1.04 | 10.06 |
| 6.00 | 71.80 | 6.63 | 5.45 | 1.81 | | 9.17 |
| 8.00 | 66.04 | 4.99 | 4.15 | 0.77 | | 6.92 |
| 10.00 | 50.58 | | | | | |

TABLE 5

Ex. 2 RESIDUAL MONOMERS (umoles/g)

| Cure Time (mins) | NVP | HEMA | TEGDMA | Norbloc | CGI 819 | OH-mPDMS |
|---|---|---|---|---|---|---|
| 0.00 | 4386.23 | 508.60 | 17.25 | 62.66 | 5.04 | 604.57 |
| 0.25 | 4515.93 | 441.52 | 13.20 | 55.55 | 3.99 | 548.76 |
| 0.50 | 4509.28 | 381.39 | 10.58 | 49.31 | 3.08 | 488.62 |
| 1.00 | 4327.69 | 277.76 | 6.48 | 35.46 | 1.60 | 373.43 |
| 2.00 | 4083.51 | 132.44 | 2.51 | 17.04 | 0.48 | 191.32 |
| 4.00 | 3361.70 | 39.99 | 1.05 | 2.62 | 0.05 | 60.85 |
| 6.00 | 3149.41 | 33.74 | 0.94 | 1.14 | | 55.44 |
| 8.00 | 2896.87 | 25.37 | 0.72 | 0.48 | | 41.86 |
| 10.00 | 2218.40 | | | | | |

TABLE 6

| Cure Time | NVP Log[A]/[A₀] | HEMA Log[A]/[A₀] | TEGDMA Log[A]/[A₀] | Norblock Log[A]/[A₀] | CGI 819 Log[A]/[A₀] | OH-mPDMS Log[A]/[A₀] |
|---|---|---|---|---|---|---|
| 0.25 | 0.0127 | −0.0614 | −0.1164 | −0.0523 | −0.1017 | −0.0421 |
| 0.50 | 0.0120 | −0.1250 | −0.2122 | −0.1041 | −0.2136 | −0.0925 |
| 1.00 | −0.0058 | −0.2627 | −0.4253 | −0.2473 | −0.4997 | −0.2092 |
| 2.00 | −0.0311 | −0.5844 | −0.8371 | −0.5656 | −1.0250 | −0.4997 |
| 4.00 | −0.1155 | −1.1044 | −1.2146 | −1.3784 | −1.9814 | −0.9972 |
| 6.00 | −0.1439 | −1.1783 | −1.2634 | −1.7418 | | −1.0377 |
| 8.00 | −0.1802 | −1.3021 | −1.3814 | −2.1130 | | −1.1596 |
| 10.00 | −0.2961 | | | | | |

TABLE 7

Ex. 2

| Component | Time Points | $R^2$ | Slope | k (min⁻¹) | Half-life (t½), min |
|---|---|---|---|---|---|
| NVP | 0.25-8 min | 0.973 | −0.0265 | 0.0610 | 11.36 |
| HEMA | 0.25-4 min | 0.998 | −0.2810 | 0.6471 | 1.07 |
| TEGDMA | 0.25-4 min | 0.963 | −0.2951 | 0.6796 | 1.02 |
| Norblock | 0.25-4 min | 0.993 | −0.3568 | 0.8217 | 0.84 |
| CGI 819 | 0.25-4 min | 0.999 | −0.5037 | 1.1600 | 0.60 |
| OH-mPDMS | 0.25-4 min | 0.999 | −0.2582 | 0.5946 | 1.17 |

TABLE 8

CE 2

| Component | Time Points | $R^2$ | Slope | k (min⁻¹) | Half-life (t₁/₂), min |
|---|---|---|---|---|---|
| DMA | 0.25-8 min | 0.975 | −0.1496 | 0.3445 | 2.01 |
| HEMA | 0.25-4 min | 0.978 | −0.2167 | 0.4991 | 1.39 |

TABLE 8-continued

CE 2

| Component | Time Points | $R^2$ | Slope | k (min⁻¹) | Half-life (t₁/₂), min |
|---|---|---|---|---|---|
| TEGDMA | 0.25-4 min | 0.971 | −0.2254 | 0.5191 | 1.34 |
| Norblock | 0.25-4 min | 0.976 | −0.1873 | 0.4314 | 1.61 |
| CGI 819 | 0.25-4 min | 0.981 | −0.3088 | 0.7112 | 0.97 |
| OH-mPDMS | 0.25-4 min | 0.988 | −0.1814 | 0.4178 | 1.66 |

TABLE 9

| | Ex.# 2 | CE2 |
|---|---|---|
| Hydrophile (HP) | NVP | DMA |
| HP ½ life | 11.36 | 2.01 |
| Si ½ life | 1.17 | 1.66 |
| HP/Si | 9.7 | 1.2 |
| [μmol HP/μmol Si] @90% conversion of Si | 55.25 | 9.27 |

In Example 2, the half-life of the NVP is nearly ten times slower (11.36 minutes) than the half-lives for the other monomers HEMA (1.07) and OH-mPDMS (1.17). In Comparative Example 1, the half-life of the DMA (2.01) is nearly the same as the half life of the silicone-containing component, OH-mPDMS (1.66). It is believed that the difference in wettability between the formulations of Example 1 and Comparative Example 1 is due to the substantially slower polymerization of the slow-reacting hydrophilic monomer in Example 1 (NVP) as compared to the hydrophilic monomer in Comparative Example 1 (DMA). Table 9 also shows that at 90% conversion of the silicone monomer, the molar ratio of the unreacted slow-reacting hydrophilic monomer NVP, compared to the unreacted silicone (mPDMS), is 55.25 for NVP, and only 9.27 for the DMA system. The NVP containing system displays improved wettability, as measured by contact angle, and increased oxygen permeability. The modulus of the DMA-containing formulation was substantially lower, which is believed to be an indication that the DMA and silicone monomers are more randomly incorporated in network. NVP system is believed to have larger blocks of silicone and NVP. Moreover the ratio of the kinetic half lives for the Comparative Example 2 system containing DMA as the hydrophile (1.21) is insufficient to provide a wettable lens. The ratio of molar concentrations of DMA and HO-PDMS for Comparative Example 1 was less than 10 (9.74).

Examples 3-5 and Comparative Example 3

The preparation described in Example 1 and kinetics evaluation described in Example 2 were repeated for the formulations listed in Table 10 below. The formulations for Example 2 and Comparative Example 2 are listed in Table 10 for convenience. Tables 11-14 show a summary of the calculated kinetics data for Examples 3-5 and Comparative Example 3, and Table 15 shows the ratios of slow hydrophilic component to the silicone component. The kinetics data for Example 2 and Comparative Example 2 is shown in Tables 5 and 6, above.

TABLE 10

| Comp. | Ex. 2 | Ex. 3 | CE2 | CE3 | Ex. 4 | Ex. 5 |
|---|---|---|---|---|---|---|
| OH-mPDMS | 40 | 40 | 40 | 40 | 0 | 0 |
| SA2 | 0 | 0 | 0 | 0 | 41 | 40 |
| NVP | 50.5 | 50.5 | 0 | 0 | 51.5 | 50.5 |
| DMA | 0 | 0 | 50.5 | 50.5 | 0 | 0 |
| HEMA | 6.75 | 8.75 | 6.75 | 8.75 | 6.75 | 6.75 |
| TEGDMA | 0.5 | 0.5 | 0.5 | 0.5 | 0.5 | 0.5 |
| Norblock | 2 | 0 | 2 | 0 | 0 | 2 |
| CGI 819 | 0.25 | 0.25 | 0.25 | 0.25 | 0.25 | 0.25 |

TABLE 11

Summary of Example 3 Kinetic Calculations

| Component | Time Points | $R^2$ | Slope | k (min$^{-1}$) | Half-life (t½), min |
|---|---|---|---|---|---|
| NVP | 0.25-4 min | 0.869 | −0.1133 | 0.2609 | 2.66 |
| HEMA | 0.25-8 min | 0.869 | −0.2911 | 0.6704 | 1.03 |
| TEGDMA | 0.25-4 min | 0.998 | −0.5114 | 1.1778 | 0.59 |
| CGI 819 | 0.25-4 min | 1.000 | −0.5228 | 1.2040 | 0.58 |
| OH-mPDMS | 0.25-2 min | 0.987 | −0.3080 | 0.7093 | 0.98 |

TABLE 12

Summary of Comparative Example 3 Kinetics Calculations

| Component | Time Points | $R^2$ | Slope | k (min$^{-1}$) | Half-life (t½), min |
|---|---|---|---|---|---|
| DMA | 0.25-2 min | 0.993 | −0.1736 | 0.3998 | 1.73 |
| HEMA | 0.25-1 min | 0.989 | −0.3734 | 0.8599 | 0.81 |
| TEGDMA | 0.25-2 min | 0.993 | −0.5279 | 1.2158 | 0.57 |
| CGI 819 | 0.25-2 min | 0.991 | −0.5106 | 1.1759 | 0.59 |
| OH-mPDMS | 0.25-1 min | 0.987 | −0.3262 | 0.7512 | 0.92 |

TABLE 13

Summary of Example 4 Kinetics Calculations

| Component | Time Points | $R^2$ | Slope | k (min$^{-1}$) | Half-life (t½), min |
|---|---|---|---|---|---|
| NVP | 0.25-1 min | 0.944 | −0.1839 | 0.4235 | 1.64 |
| HEMA | 0.25-2 min | 0.970 | −1.1455 | 2.6381 | 0.26 |
| TEGDMA | 0.25-2 min | 0.942 | −1.0470 | 2.411 | 0.29 |
| CGI 819 | 0.25-4 min | 0.959 | −0.3555 | 0.8187 | 0.85 |
| SA2 | 0.25-2 min | 0.913 | −0.7599 | 1.7500 | 0.40 |

TABLE 14

Summary of Example 5 Kinetics Calculations

| Component | Time Points | $R^2$ | Slope | k (min$^{-1}$) | Half-life (t½), min |
|---|---|---|---|---|---|
| NVP | 0.25-1 min | 0.891 | −0.0630 | 0.1451 | 4.78 |
| HEMA | 0.25-2 min | 0.947 | −1.2118 | 2.7908 | 0.25 |
| TEGDMA | 0.25-2 min | 0.886 | −2.1365 | 4.9204 | 0.14 |
| Norbloc | 0.25-2 min | 0.981 | −1.4710 | 3.3877 | 0.20 |
| CGI 819 | 0.25-2 min | 0.988 | −0.4677 | 1.0771 | 0.64 |
| SA2 | 0.25-2 min | 0.712 | −0.4544 | 1.0465 | 0.66 |

TABLE 15

| Ex. # | 2 | 3 | CE2 | CE3 | 4 | 5 |
|---|---|---|---|---|---|---|
| Norbloc | Y | N | Y | N | N | Y |
| Hydrophile | NVP | NVP | DMA | DMA | NVP | NVP |
| HP ½ life | 11.36 | 2.66 | 2.01 | 1.73 | 1.64 | 4.78 |
| Silicone | HO-mPDMS | HO-mPDMS | HO-mPDMS | HO-mPDMS | SA2 | SA2 |
| Si ½ life | 1.17 | 0.98 | 1.66 | 0.92 | 0.4 | 0.66 |
| HP/Si | 9.7 | 2.7 | 1.2 | 1.88 | 4.1 | 7.24 |
| [µmol HP/µmol Si] @90% conversion | 55.25 | 40.21 | 9.27 | 8.99 | 55.79 | 60.23 |

Considering the data in Table 15, including a UV absorbing compound in a photoinitiated reactive monomer mixture causes the half life of the slow-reacting hydrophilic monomer NVP to increase by between 60 and 400%, while the half life of DMA increases marginally from 1.73 to 2.01 (16%). The half life of the HO-mPDMS was also increased. The half life of the SA2 silicone decreased upon addition of the UV absorber, Norbloc, but the decrease was not enough to offset the substantial increase in the half life of the NVP. Comparing Comparative Example 2 (formulation containing DMA and Norbloc) to Comparative Example 3 (formulation containing DMA without Norbloc), it can be seen that the inclusion of Norbloc in a DMA-containing formulation slowed the reaction rate for the crosslinker TEGDMA and more than doubled its half life. In the DMA/Norbloc-containing formulation, this meant that the crosslinker had a reactivity rate much more similar to the hydrophilic monomer and silicone-containing component. Even though the inclusion of a UV absorber such as Norbloc slowed the reaction rate for TEGDMA, it was still faster (4.92) than both the hydrophilic monomer (0.145) and silicone-containing component (1.05).

Contact lenses were made from the Formulations of Examples 3-5 and Comparative Example 3 using the method described in Example 2. The properties of the lenses were measured and are shown in Table 16, below.

TABLE 16

| Ex. # | % H$_2$O | % Haze | DCA | Mod. (psi) | Elong. (%) | Dk |
|---|---|---|---|---|---|---|
| 2 | 58.4 (0.2) | 4 (0) | 44 (4) | 103 (11) | 220 (36) | 75 |
| 3 | 66.6 (0.1) | 24 (1) | 50 (3) | 63 (8) | 192 (76) | 79 |
| CE2 | 59.8 (0.1) | 5 (1) | 127 (14) | 54 (7) | 227 (52) | 49 |
| CE3 | 58.1 (0.2) | 3 (1) | 132 (7) | 78 (7) | 199 (39) | 49 |
| 4 | 67 (0.2) | 67 (2) | 51 (3) | 64 (7) | 229 (97) | 82 |
| 5 | 65.5 (0.1) | 8 (1) | 68 (7) | 105 (9) | 242 (49) | 57 |

The lenses of Examples 2 through 5 show desirable haze and wettability, as well as a balance of other desirable properties. Each of these Examples had ratios of the slow-reacting hydrophilic monomer half life:silicone-containing component half life greater than about 2. Comparative Examples 2 and 3 had half life ratios of below 2 (1.2 and 1.88 respectively). Thus, half life ratios greater than about 2, and in some embodiments greater than about 3 are desirable to provide desirable wettability.

Comparing the modulii of Comparative Example 2 (54 psi, with Norbloc) and Comparative Example 3 (78 psi without Norbloc) it can be seen that the change in the reactivity rate for TEGDMA caused by the inclusion of Norbloc was sufficient to decrease crosslinking in the network of the resulting polymer. Thus, in additional to changing the amount of crosslinker, one can also choose a crosslinker with a different reactivity ratio to achieve a desired polymer structure and modulus. The same behavior is also observed comparing the SA2/NVP-containing formulations of Examples 4 and 5.

Examples 6-10

The level of BHT and initiator was varied as shown in Table 17. In Example 102 wt % VINAL, was added to the formulation of Example 6.

TABLE 17

| | Ex# | | | | |
|---|---|---|---|---|---|
| | 6 | 7 | 8 | 9 | 10 |
| [BHT] ug/g | 1429 | 166 | 166 | 166 | 1429 |
| mPDMS 1000 | 15 | 15 | 15 | 15 | 15 |
| OH-mPDMS, n = 4 | 25 | 25 | 25 | 25 | 25 |
| NVP | 50.5 | 50.5 | 50.38 | 50.25 | 48.5 |
| HEMA | 6.75 | 6.75 | 6.75 | 6.75 | 6.54 |
| VINAL | 0 | 0 | 0 | 0 | 2 |
| TEGDMA | 0.5 | 0.5 | 0.5 | 0.5 | 0.5 |
| Norbloc | 2 | 2 | 2 | 2 | 2 |
| CGI 819 | 0.25 | 0.25 | 0.37 | 0.5 | 0.25 |

The kinetics for the two formulations were measured and calculated as described in Example 1, and contact lenses were made as described in Example 2. The kinetics for the formulations are shown in Tables 18-24, and the lens properties are shown in Table 25.

TABLE 18

Example 6

| Component | Time Points | $R^2$ | Slope | k (min$^{-1}$) | Half-life (t½), min |
|---|---|---|---|---|---|
| NVP | 0.25-8 min | 0.975 | −0.0267 | 0.0615 | 11.27 |
| HEMA | 0.25-4 min | 0.993 | −0.2044 | 0.4707 | 1.47 |
| TEGDMA | 0.25-2 min | 0.947 | −0.3171 | 0.7303 | 0.95 |
| Norbloc | 0.25-4 min | 0.999 | −0.2441 | 0.5622 | 1.23 |
| CGI 819 | 0.25-4 min | 1.000 | −0.5438 | 1.2524 | 0.55 |
| OH-mPDMS | 0.25-4 min | 0.997 | −0.1885 | 0.4341 | 1.60 |
| mPDMS 1000 | 0.25-4 min | 0.997 | −0.1515 | 0.3489 | 1.99 |

TABLE 19

Example 7

| Component | Time Points | $R^2$ | Slope | k (min$^{-1}$) | Half-life (t½), min |
|---|---|---|---|---|---|
| NVP | 0.25-8 min | 0.989 | −0.0294 | 0.0677 | 10.24 |
| HEMA | 0.25-4 min | 0.997 | −0.2527 | 0.5820 | 1.19 |
| TEGDMA | 0.25-2 min | 0.989 | −0.4923 | 1.1338 | 0.61 |
| Norbloc | 0.25-4 min | 0.999 | −0.3536 | 0.8143 | 0.85 |
| CGI 819 | 0.25-4 min | 1.000 | −0.5228 | 1.2040 | 0.58 |
| OH-mPDMS | 0.25-4 min | 0.999 | −0.2499 | 0.5755 | 1.20 |
| mPDMS 1000 | 0.25-2 min | 0.996 | −0.1474 | 0.3395 | 2.04 |

TABLE 20

Example 8

| Component | Time Points | $R^2$ | Slope | k (min$^{-1}$) | Half-life (t½), min |
|---|---|---|---|---|---|
| NVP | 0.25-8 min | 0.990 | −0.0381 | 0.0877 | 7.90 |
| HEMA | 0.25-4 min | 0.985 | −0.3395 | 0.7819 | 0.89 |
| TEGDMA | 0.25-4 min | 0.946 | −0.3549 | 0.8173 | 0.85 |
| Norblock | 0.25-4 min | 0.980 | −0.5042 | 1.1612 | 0.60 |
| CGI 819 | 0.25-4 min | 0.999 | −0.4793 | 1.1038 | 0.63 |
| OH-mPDMS | 0.25-4 min | 0.989 | −0.3222 | 0.7420 | 0.93 |
| mPDMS 1000 | 0.25-4 min | 0.993 | −0.2765 | 0.6368 | 1.09 |

TABLE 21

Example 9

| Component | Time Points | $R^2$ | Slope | k (min$^{-1}$) | Half-life (t½), min |
|---|---|---|---|---|---|
| NVP | 0.25-8 min | 0.887 | −0.0611 | 0.1407 | 4.92 |
| HEMA | 0.25-4 min | 0.924 | −0.4627 | 1.0656 | 0.65 |
| TEGDMA | 0.25-4 min | 0.852 | −0.4986 | 1.1483 | 0.60 |
| Norblock | 0.25-4 min | 0.985 | −0.6741 | 1.5525 | 0.45 |
| CGI 819 | 0.25-4 min | 1.000 | −0.4326 | 0.99628 | 0.70 |
| OH-mPDMS | 0.25-4 min | 0.940 | −0.4831 | 1.1126 | 0.62 |
| mPDMS 1000 | 0.25-4 min | 0.989 | −0.4703 | 1.0831 | 0.64 |

TABLE 22

Example 10

| Component | Time Points | $R^2$ | Slope | k (min$^{-1}$) | Half-life (t½), min |
|---|---|---|---|---|---|
| VINAL | 0.25-18 min | 0.904 | −0.0126 | 0.0290 | 23.88 |
| NVP | 0.25-8 min | 0.949 | −0.0273 | 0.0629 | 11.02 |
| HEMA | 0.25-2 min | 0.979 | −0.3082 | 0.7098 | 0.98 |
| TEGDMA | 0.25-2 min | 0.984 | −0.4253 | 0.9795 | 0.71 |
| Norbloc | 0.25-2 min | 0.975 | −0.2924 | 0.6734 | 1.03 |
| CGI 819 | 0.25-4 min | 1.000 | −0.4882 | 1.1243 | 0.62 |
| OH-mPDMS | 0.25-2 min | 0.971 | −0.2819 | 0.6492 | 1.07 |
| mPDMS 1000 | Not Measured | | | | |

TABLE 23

| | Ex. # | | | | |
|---|---|---|---|---|---|
| | 6 | 7 | 8 | 9 | 10 |
| [BHT] ug/g | 9324 | 901 | 901 | 901 | 9324 |
| [CGI 819] | 0.25 | 0.25 | 0.37 | 0.5 | 0.25 |
| NVP ½ life | 11.27 | 10.24 | 7.90 | 4.92 | 11.02 |
| mPDMS ½ life | 1.99 | 2.04 | 1.09 | 0.64 | ** |
| OH-mPDMS ½ life | 1.60 | 1.02 | 0.93 | 0.62 | 1.07 |
| NVP/MPDMS | 5.7 | 5.0 | 7.3 | 7.7 | ** |
| NVP/OH-mPDMS | 7.0 | 8.5 | 8.5 | 7.9 | 10.3 |
| VINAL/HO-PDMS | ** | ** | ** | ** | 22.3 |
| [μmol NVP]/[μmol mPDMS] @90% conversion | 211.45 | 233.18 | 273.5 | 251.9 | XX |
| [μmol NVP]/[μmol HO-mPDMS] @90% conversion | 94.71 | 83.6 | 92 | 99 | 68.57 |

** Not applicable
XX not measured.

TABLE 24

| | Ex. # | | | | |
|---|---|---|---|---|---|
| | 6 | 7 | 8 | 9 | 10 |
| % H$_2$O | 59.1 (0.1) | 60.0 (0.2) | 61.3 (0.2) | 63.6 (0.2) | 61.3 (0.2) |
| % Haze | 3 (1) | 5 (1) | 4 (1) | 5 (0) | NT |
| DCA | 49 (2) | 47 (3) | 52 (4) | 56 (5) | 51 (3) |
| Mod. (psi) | 92 (10) | 84 (10) | 65 (9) | 66 (7) | 84 (12) |
| Elong. (%) | 188 (67) | 194 (64) | 197 (25) | 163 (61) | 149 (61) |
| Dk | 86.7 | 90.7 | 82.8 | 82.3 | 90.4 |
| Lipocalin (µg/lens) | 3.16 (0.6) | 3.37 (0.2) | NT | NT | 2.98 (0.3) |
| Total lipids (µg/lens) | 22.7 (2.9) | 23 (1.9) | NT | NT | 13.2 (1.9) |
| Lysozyme (µg/Lens) | 5.6 (0.9) | NT | NT | NT | 39 (6.2) |
| Lysozyme Activity (%) | 68 (2.7) | NT | NT | NT | 78.7 (2.5) |
| PQ1 Uptake (µg/mL) | 7.4 (0.4) | NT | NT | NT | 7.1 (0.1) |

All the lenses of Examples 6-10 have half life ratios greater than about 5, and all display desirably low contact angles (less than 60°), very low haze (less than 10) and desirable oxygen permeabilities greater than 80. The lenses of Examples 6-10 also have concentration ratios of the slow-reacting hydrophilic monomer to the silicone-containing components at 90% conversion of greater than about 83. Comparing Examples 6 and 7 shows that decreasing the inhibitor concentration from 1429 µg/g to 166 µg/g reduces the modulus slightly, but has a negligible impact on the other measured lens properties. Comparing Examples 7-9, decreases both the modulus and the Dk and increases the water content of the resultant lenses, particularly comparing Examples 7 and 9. This would suggest that the incorporation of the HO-PDMS is having a larger effect on the Dk than the incorporation of the mPDMS, as the kinetic ratio of NVP to HO-PDMS is trending in the same direction as the Dk for Examples 7-9.

Example 10 contained 2 wt % of VINAL, an ionic amide containing vinyl ether. The kinetics data in Table 23 confirms that VINAL is a slow reacting monomer. The lenses of Example 10 displayed greatly improved lysozyme uptake (39 µg/lens) compared to Example 6 (5.6 µg/lens), which contained no VINAL. The lens of Example 10 also displayed PQ-1 uptake which was no different than Example 6. PQ-1 is a cationic preservative which is present in a number of cleaning and care solutions. Contact lenses with blocks of anionic repeating units, or contact lenses with coatings of anionic polymers, can display markedly increased PQ-1 uptake values. The low value for Example 10 indicates that the VINAL was generally randomly polymerized with the NVP.

Examples 11-17

A series of lens formulations were formed from the following reactive components:
38.5 wt % mPDMS
NVP
hydroxyalkyl methacrylate, shown in Table 25
1 wt % TEGDMA
0.25 CGI 819

The amount of hydroxyalkyl (meth)acrylate and NVP were varied to provide molar ratios of the hydroxyalkyl (meth)acrylate:NVP of about 0.2. GMMA has two hydroxyl groups. Accordingly, formulations having two different concentrations of GMMA were prepared, Example 16 (13.23 wt % GMMA, 0.408 ratio, counting both hydroxyls) and Example 17 (6.62 wt % GMMA, 0.204, counting two hydroxyl).

The reactive components were mixed with a diluent (50% TAA/50% DA) in a ratio of 80 wt % reactive components:20 wt % diluent. Examples 15 and 16 produce hazy reaction mixtures which were not cured into lenses. Examples 11-14 and 17 produced clear reaction mixtures which were cast into lenses using the following the procedure. The reaction mixture was degassed by applying vacuum at ambient temperature for about 17(±3) minutes. The reaction mixture was then dosed into thermoplastic contact lens molds (front curves made from Zeonor, and back curves from polypropylene), The BC was placed on the FC mold to produce 8 BC/FC assemblies in a pallet. Pallets were placed on a mirrored surface and a quartz plate (12.50 mm×6.25 mm×0.50 mm) was placed over each pallet. The lenses were cured for about 15 minutes at 45° C., under a nitrogen atmosphere, using Philips TL 20 W/03 T fluorescent bulbs and 4-5 mW/cm$^2$.

Lenses were released in 50/50 IPA/water, extracted in 70/30 IPA/water and subsequently equilibrated in de-ionized water. Lenses were transferred into vials containing borate buffered saline for at least 24 hours and then autoclaved at 122° C. for 30 minutes. Lens properties were measured and are reported in Table 63, below.

TABLE 25

| Example | 11 | 12 | 13 | 14 | 15 | 16 | 17 |
|---|---|---|---|---|---|---|---|
| Component | HEMA | HPMA | HBMA | DMHEMA | HEAA | GMMA | GMMA |
| [NVP] wt % | 47.5 | 47.5 | 45.18 | 45.18 | 48.75 | 45.01 | 51.63 |
| [HOMA] wt % | 10.75 | 10.75 | 13.07 | 13.07 | 9.50 | 13.23 | 6.62 |
| HOMA:NVP (molar) | 0.193 | 0.174 | 0.203 | 0.203 | 0.188 | 0.408 | 0.204 |
| % H$_2$O | 59.1 (0) | 58.9 (0.1) | 54.5 | 60.4 | NT* | NT | 62.6 |
| % Haze | 8 (0) | 16 (0) | 8 | 15 | NT* | NT* | 12 |
| DCA | 60 (7) | 63 (5) | 46 | 70 | NT* | NT* | 49 |
| MOD (psi) | 79.9 (1.9) | 73.4 (1.4) | 120.5 | 68.7 | NT* | NT* | 70.4 |
| Elong (%) | 196.2 (24.6) | 230.1 (1.8) | 179.3 | 206.5 | NT* | NT* | 203.5 |
| Dk | 89.1 | 93.4 | 93.4 | 90 | NT* | NT* | 85.3 |

NT* = Not Tested

Comparing Examples 16 and 17, it can be seen that when the molar amount of GMMA was adjusted to account for both hydroxyls, clear lenses were formed. It is believed that Example 15, which included HEAA as the hydroxyalkyl (meth)acrylate, did not provide wettable lenses because the HEAA contains two polar groups, the amide and hydroxyl groups, making the HEAA more polar than the other hydroxyalkyl (meth)acrylates used in Examples 11-14 and 16-17. It is believed that the increased polarity of HEAA caused compatibility issues with the mPDMS. However, HEAA has the potential to work with more polar silicones, such as SiMAA, OH-mPDMS, N-(2,3-dihydroxypropane)-N'-(propyl tetra(dimethylsiloxy)dimethylbutylsilane)acrylamide. Thus, a variety of hydroxylalkyl (meth)acrylate compounds can be used to form the hydrogels of the present invention.

Examples 18-21

Additional reaction mixtures were made varying the diluents system used and the siloxane components as shown in Tables 64 and 65, below. All mixtures were formed using 80 wt % reactive components and 20 wt % diluents. The lenses were molded, cured, processed and sterilized according to the procedure described in Example 27, above. The lens properties were measured and are shown in Tables 26 and 27.

TABLE 26

|  | Ex 18 | Ex 19 | Ex 20 | Ex 21 |
|---|---|---|---|---|
| mPDMS | 20 | 20 | 20 | 20 |
| TRIS | 18.5 | 18.5 | 18.5 | 18.5 |
| NVP | 47.5 | 47.5 | 47.5 | 47.5 |
| HEMA | 10.75 | 10.75 | 10.75 | 10.75 |
| TEGDMA | 1 | 1 | 1 | 1 |
| Norbloc | 2 | 2 | 2 | 2 |
| CGI819 | 0.25 | 0.25 | 0.25 | 0.25 |
| Diluent | 1:1 EtOAc:EtOH | TAA | D3O | 1:1 TAA:DA |
| EWC | 46.0 ± 1.6% | 55.5 ± 0.1% | 58.9 ± 0.1% | 57.4 ± 0.1% |
| Haze | 50 ± 19 | 10 ± 2 | 12 ± 1 | 7 ± 0 |
| DCA | NT | NT | 66 ± 4° | 69 ± 6° |
| Modulus | 100 ± 13 psi | 83 ± 9 psi | 80 ± 7 psi | 88 ± 6 psi |
| Elongation | 305 ± 105% | 330 ± 49% | 307 ± 39% | 285 ± 73% |
| Dk | NT | 80 | 64 | 75 |

NT = Not tested

TABLE 27

|  | Ex22** | Ex 23 | Ex 24** | Ex 25 |
|---|---|---|---|---|
| mPDMS | 38.5 | 38.5 | 38.5 | 38.5 |
| NVP | 47.5 | 47.5 | 47.5 | 47.5 |
| HEMA | 10.75 | 10.75 | 10.75 | 10.75 |
| TEGDMA | 1 | 1 | 1 | 1 |
| Norbloc | 2 | 2 | 2 | 2 |
| CGI819 | 0.25 | 0.25 | 0.25 | 0.25 |
| diluent | 1:1 EtOAc:EtOH | TAA | D3O | 1:1 TAA:DA |
| EWC | ** | 56.3 ± 0.2% | ** | 59 ± 0.1% |
| Haze | ** | 8 ± 0 | ** | 9 ± 1 |
| DCA | ** | 74 ± 2° | ** | 54 ± 3° |
| Modulus | ** | 62 ± 9 psi | ** | 70 ± 5 psi |
| % Elongation | ** | 252 ± 63% | ** | 245 ± 62% |
| Dk | ** | 107 | ** | 91 |

** Blends were immiscible

The blends of Examples 22 and 24 were immiscible and were not cast into lenses. These Examples show that a wide range of diluents may be used to form the lenses of the present invention. These examples also show that secondary alcohols provide formulations with a desirable balance of properties, including clarity and modulus, when photocured.

Examples 26-31

Lenses were made from the formulations in Table 28 with concentration of the reactive components, adding up to 100 wt %. No diluent was used.

The reaction mixtures were degassed by applying vacuum at ambient temperature for about 17(±3) minutes. The reaction mixture (75 μL) was then dosed at room temperature and <0.1% $O_2$, into thermoplastic contact lens molds (FC—Zeonor, BC Polypropylene) which had been degassed in $N_2$ box at RT (Compartment 1, FIG. 1) for a minimum of 12 hours prior to dosing. The BC was placed on the FC mold and the lenses were moved into Compartment 2 and cured for 20 minutes, at an intensity of 4-5 mW/cm$^2$, <0.1% $O_2$, and 62-65° C.

The molds for all the lenses were mechanically separated and the lenses remained in the FC. The lenses were dry released by pressing on the back of the front curve. Lenses were extracted in DI water
All lenses were stored in borate buffered packing solution in lens vials and sterilized at 122° C. for 30 minutes.

The ability of the lenses to recover from mechanical stress, such as folding was evaluated. A crease was generated in each lens by placing a folded unsterilized lens between two rectangular glass plates (12.5 cm×6.3 cm×0.5 cm (~113 g)) for five minutes. The lens was subsequently sterilized and visually inspected using a DL2 (17.5×) and Optimec, to discern the level of recovery.

Increasing degrees of creasing/stress were created in unsterilized lenses by using 2, 3, 4 or 5 top plates. The results of the stress test are shown in Table 30.

The stress test values for three commercial lenses, ACUVUE OASYS with HYDRACLEAR Plus, Biofinity and Clariti lenses are shown as controls.

The properties of the lenses were measured and are shown in Table 29.

TABLE 28

| Ex. # | 26 | 27 | 28 | 29 | 30 | 31 |
|---|---|---|---|---|---|---|
| mPDMS 1000 | 19.35 | 19.35 | 19.35 | 19.35 | 19.35 | 19.35 |
| OH-mPDMS (n = 4) | 27.50 | 27.50 | 27.50 | 27.50 | 27.50 | 27.50 |
| VMA | 0.00 | 8.00 | 12.00 | 22.00 | 32.00 | 44.00 |
| HEMA | 6.50 | 6.50 | 6.50 | 6.50 | 6.50 | 6.50 |
| NVP | 44.00 | 36.00 | 32.00 | 22.00 | 12.00 | 0.00 |
| TEGDMA | 0.20 | 0.20 | 0.20 | 0.20 | 0.20 | 0.20 |
| TAG | 0.20 | 0.20 | 0.20 | 0.20 | 0.20 | 0.20 |
| Norbloc | 1.75 | 1.75 | 1.75 | 1.75 | 1.75 | 1.75 |
| CGI 819 | 0.50 | 0.50 | 0.50 | 0.50 | 0.50 | 0.50 |
| Diluent | 0.00 | 0.00 | 0.00 | 0.00 | 0.00 | 0.00 |

TABLE 29

| | | | | Mechanicals | | | | |
|---|---|---|---|---|---|---|---|---|
| Lens | % $H_2O$ | % Haze | DCA | Mod. (psi) | Elong. (%) | Dk | Res. NVP | Res. VMA |
| 26 | 55 (0) | 6 (0) | 55 (3) | 95 (6) | 270 (34) | 96 | 0.8 (0.02) | N/A |
| 27 | 56 (0) | 6 (0) | 67 (5) | 104 (7) | 233 (49) | 100 | NT | NT |
| 28 | 56 (0) | 5 (0) | 58 (4) | 100 (8) | 258 (36) | 100 | 0.51 (0.02) | 1.15 (0.08) |
| 29 | 58 (0) | 6 (0) | 56 (9) | 91 (9) | 223 (54) | 96 | 0.4 (0.04) | 2.2 (0.2) |
| 30 | 58 (0) | 7 (0) | 56 (5) | 92 (10) | 260 (62) | 103 | 0.3 (0.01) | 2.98 (0.06) |
| 31 | 58 (0) | 13 (2) | 50 (10) | 86 (7) | 262 (54) | 106 | N/A | 4.52 (0.61) |

TABLE 30

Post Sterilization Inspection - DL2 (17.5X) and Optimec

| Ex# | Control (0 Plate) | 1 Plate | 2 Plates | 3 Plates | 4 Plates | 5 Plates |
|---|---|---|---|---|---|---|
| 26 | G | G | G | G | G | G |
| 27 | G | G | G | G | G | G |
| 28 | G | G | G | G | G | G |
| 28 | G | G | G | G | G | G |
| 30 | G | G | G | G | G | G |
| 31 | G | G | G | G | G | G |

Examples 32-34

Reactive mixtures were formed from the components listed in Table 31 and degassed by applying vacuum at ambient temperature for about 17(±3) minutes. The reaction mixture (75 μL) was then dosed at room temperature and <0.1% $O_2$, into thermoplastic contact lens molds (FC—Zeonor, BC Polypropylene) which had been degassed in $N_2$ box at RT (Compartment 1, FIG. 1) for a minimum of 12 hours prior to dosing. The BC was placed on the FC mold to produce 8 BC/FC assemblies in a pallet. Eight pallets were prepared, moved into the cure compartment (Compartment 2) and placed on a mirrored surface. A quartz plate (12.50 mm×6.25 mm×0.50 mm) was placed over each pallet and the lenses were and cured for 20 minutes, at an intensity of 4-5 mW/cm², <0.1% $O_2$, and 62-65° C.

The molds for all the lenses were manually demolded (lenses remained in FC). Lenses were released in 50/50 IPA/water, extracted in 50/50 IPA/water and subsequently equilibrated in de-ionized water. Lenses were transferred into vials containing borate buffered saline for at least 24 hours and then autoclaved for 1, 3, 6 and 9 cycles at 122° C. for 30 minutes. Water content and modulus were measured after each sterilization cycle.

The resulting lenses were very clear, and felt lubricious when rubbed between the thumb and forefinger.

TABLE 31

| Component | E. 32 | 33 | 34 |
|---|---|---|---|
| Tris | 19.10 | 19.10 | 19.10 |
| OH-mPDMS | 25.00 | 25.00 | 25.00 |
| NVP | 46.50 | 44.00 | 45.15 |
| HEMA | 6.75 | 6.75 | 6.75 |
| TEGDMA | 0.20 | 0.20 | 0.20 |
| TAC | 0.20 | 0.20 | 0.20 |
| Norbloc | 1.75 | 1.75 | 1.75 |
| VINAL | 0.00 | 2.50 | 0.00 |
| MAA | 0.00 | 0.00 | 1.35 |
| CGI 819 | 0.50 | 0.50 | 0.50 |
| Diluent | 0.00 | 0.00 | 0.00 |
| TAM | 100.00 | 100.00 | 100.00 |

TABLE 32

| Ex# | # Cycles | % $H_2O$ | % ΔH2O | Mod. | % ΔMod. | Elong. | % ΔElong. |
|---|---|---|---|---|---|---|---|
| 32 | 1 | 57 | 0 | 139.0 | 0 | 223.8 | 0 |
|  | 3 | 57 | 0 | 139.9 | 0.6 | 200.4 | −11 |
|  | 6 | 58 | 1.8 | 157.0 | 13 | 123.4 | −45 |
|  | 9 | 59 | 3.5 | 158.1 | 14 | 95.5 | −57 |
| 33 | 1 | 60 | 0 | 129.3 | 0 | 200.9 | 0 |
|  | 3 | 60 | 0 | 132.2 | 2 | 191.2 | −5 |
|  | 6 | 61 | 2 | 112.3 | −13 | 151 | −25 |
|  | 9 | 61 | 2 | 142.5 | 10 | 107.9 | −46 |
| 34 | 1 | 60 | 0 | 105.3 | 0 | 230.9 | 0 |
|  | 3 | 60 | 0 | 115 | 9 | 180 | −22 |
|  | 6 | 60 | 0 | 127.6 | 21 | 102 | −56 |
|  | 9 | 59 | −2 | 170.8 | 62 | 92 | −60 |

The change in properties was calculated compared to the change after a single autoclave cycle.

The lenses of the present invention (Example 33) show thermal stability better than the non-ionic lenses of Example 32, or the lenses of Example 34, which have methacrylic acid. Thus, the present invention can provide ionic silicone hydrogel lenses which have thermal stability equal to that displayed by non-ionic lenses. The lenses of the present invention showed a less than 5% change in modulus over 3 autoclave cycles and a less than about 25% change in modulus over six autoclave cycles.

Synthetic Preparation 1: 2-hydroxybutyl methacrylate (HBMA)

A blend of 72 grams 1,2-epoxybutane (Aldrich), 0.85 g 4-methoxyphenol (Aldrich), and 6.5 g potassium hydroxide was stirred in a 500 ml round bottomed flask equipped with an addition funnel and thermocouple thermometer. 172 g methacrylic acid was added via the addition funnel, and the blend was slowly to 75° C., and stirred overnight under an air, then increased to 88° C. for 4 hours. The mixture was cooled, and 700 ml of 2.0 N NaOH was added to the mixture in a separatory funnel. The upper layer was washed with borate buffered saline three times. Ethyl ether (200 ml) was added to the combined saline washes to extract any product. The combined organic layers were dried over $NaSO_4$. The $NaSO_4$ was filtered out and the product was distilled (90-98° C./~4 mm Hg). 17.5 g product was collected, to which was added 4 mg 4-methoxyphenol. $^1$H NMR: 6.1 ppm (1H, m), 5.5 (1H, m), 4.8 (0.25H m), 4.2 (0.64 H, dd, 8.1 and 11.7 Hz), 4.0 (0.64 Hz, dd, 6.9 and 11.4 Hz), 3.6-3.8 1.26H, m), 2.3 (OH, br s), 1.9 (3H, m), 1.4-1.7 (2H, m), 0.9 (3H, m); consistent with a blend of 2-hydroxy-1-propylmethacrylate and 1-hydroxy-2-propylmethacrylate.

Synthetic Preparation 2: dimethylhydroxyethylmethacrylate

The same procedure as for HBMA was used, but substituting 1,2-epoxy-2-methylpropane for the 1,2-epoxypropane. The product was isolated by distillation at 47-48°/0.4-0.6 mm Hg. $^1$H NMR: 6.1 ppm (1H, s), 5.5 (1H, m), 4.0 (2H, s), 2.1 (OH, br s), 1.9 (3H, s), 1.2 (6H, m); consistent 2-hydroxy-2-methyl propylmethacrylate (dimethylhydroxyethylmethacrylate).

Synthetic Preparation 3: VINAL 4.82 g vinyl chloroformate was added to a mixture of 8.19 g (3-alanine (Aldrich) in 74 ml acetonitrile. The resulting mixture was refluxed for 2 hours, then cooled to room temperature and allowed to sit for 2 hours. It was filtered and solvent was removed under reduced pressure. The crude product was dissolved in 30 ml distilled water and washed three times with ethyl acetate. The combined ethyl acetate washes were washed with 50 ml deionized water. Solvent was evaporated from the combined ethyl acetate washes to yield 4.5 g product as a fluffy yellowish solid. $^1$H NMR: 7.1 ppm (dd, 1H), 5.4 ppm (br s, OH), 4.7 ppm (dd, 1H), 4.4 ppm (dd, 1H), 3.5 ppm (q, 2H), 2.6 ppm (t, 2H).

What is claimed is:

1. A silicone hydrogel comprising at least one pharmaceutical or nutraceutical component wherein said silicone hydrogel is formed from a reaction mixture comprising
   about 37 to about 75 wt % of a mixture of slow-reacting hydrophilic monomers, each having a slow-reacting hydrophilic monomer kinetic half life; said mixture of slow reacting hydrophilic monomers comprising at least one slow-reacting ionic monomer;
   at least one silicone-containing component having a silicone-containing component kinetic half life, which may be optionally substituted with at least one hydroxyl containing group; and
   at least one hydroxyl-containing component selected from said silicone-containing components substituted with at least one hydroxyl containing group, at least one hydroxyalkyl monomer, and mixtures thereof,
   wherein ratio of each of said slow-reacting hydrophilic component half lives to said silicone-containing component half life is at least 2.

2. The silicone hydrogel of claim 1 wherein said slow-reacting ionic component is selected from the group consisting of anionic components, cationic components, zwitterionic components and mixtures thereof.

3. The silicone hydrogel of claim 1 wherein said slow-reacting ionic component comprise at least one anionic component selected from the group consisting of carboxylic acids, sulfonic acids, boronic acids, phosphonic acids and their salts and mixtures thereof.

4. The silicone hydrogel of claim 1 wherein said slow-reacting ionic component comprises reactive functionality selected from the group consisting of ionic vinyl ethers, ionic vinyl amines and ionic vinyl enamines.

5. The silicone hydrogel of claim 1 wherein said slow-reacting ionic component is selected from the group consisting of 4-acrylamidobutanoic acid (ACAII), (3-acrylamidophenyl)boronic acid (APBA), 3-acrylamidopropionic acid, 5-acrylamidopentanoic acid, 3-acrylamido-3-methylbutanoic acid (AMBA), N-vinyloxycarbonyl-α-alanine, N-vinyloxycarbonyl-β-alanine (VINAL), 2-vinyl-4,4-dimethyl-2-oxazolin-5-one (VDMO), vinyl sulphonate salt, 3-((3-acrylamidopropyl)dimethylammonio)propane-1-sulfonate (AMPDAPS), 3-((3-methacrylamidopropyl)dimethylammonio)propane-1-sulfonate (MAMPDAPS); acetic acid, 2-carboxymethoxy)-, 1-ethenylester, of Formula

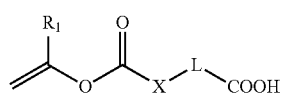

Formula Q

Where $R_1$ is H or methyl, X is O or $NR_2$, $R_2$ is H or $C_1$-$C_3$ alkyls), and L is divalent $C_{1-4}$ alkyl group; and mixtures thereof.

6. The silicone hydrogel of claim 1 wherein said slow-reacting ionic component is selected from the group consisting of N-vinyloxycarbonyl-α-alanine; N-vinyloxycarbonyl-β-alanine (VINAL); 2-vinyl-4,4-dimethyl-2-oxazolin-5-one (VDMO); vinyl sulphonate sodium salt; acetic acid, 2-carboxymethoxy)-, 1-ethenylesters of Formula Q, mixtures thereof and the like.

7. The silicone hydrogel of any of claims 1-4 wherein said slow-reacting ionic component is present in the reactive mixture in an amount below about 20 mole %.

8. The silicone hydrogel of any of claims 1-4 wherein said slow-reacting ionic component is present in the reactive mixture in an amount between about 0.5 and about 15 mole %, based upon all components in the reaction mixture.

9. The silicone hydrogel of any of claims 1-4 wherein said slow-reacting ionic component is present in the reactive mixture in an amount between about 0.5 and about 5 mole %, based upon all components in the reaction mixture.

10. The silicone hydrogel of any of claims 1-4 wherein said slow-reacting ionic component is present in the reactive mixture in an amount between about 0.5 and about 10 mole %, based upon all components in the reaction mixture.

11. The silicone hydrogel of claim 1 wherein all of said slow-reacting components have the same reactive functionality.

12. The silicone hydrogel of claim 1 wherein all of said slow-reacting components have vinyl functionality.

13. The silicone hydrogel of claim 1 wherein said reaction mixture further comprises at least one slow reacting crosslinker and at least one fast reacting crosslinker.

14. The silicone hydrogel of claim 13 wherein said slow reacting crosslinkers have only vinyl reactive functionality and said fast reacting crosslinkers have (meth)acrylate reactive functionality only.

15. The silicone hydrogel of claim 13 wherein said slow reacting crosslinker comprises triallylcyanurate and said fast reacting crosslinker is selected from the group consisting of ethylene glycol dimethacrylate, tetraethyleneglycol dimethacrylate and mixtures thereof.

16. The silicone hydrogel of claim 13 wherein said at least one slow reacting crosslinker and at least one fast reacting crosslinker are each present in said reaction mixture in amounts between about 0.4 to about 2.0 mmoles per 100 g of reactive components.

17. The silicone hydrogel of claim 13 wherein said at least one slow reacting crosslinker and at least one fast reacting crosslinker are each present in said reaction mixture in amounts between about 0.3 to about 2.0 mmol/100 g of polymerizable components.

18. The silicone hydrogel of claim 1 wherein said reactive mixture further comprises at least one reactive cationic component.

19. The silicone hydrogel of claim 18 wherein said cationic component or hydrogen bonding component is present in an amount sufficient to improve surface resilience of said hydrogel.

20. The silicone hydrogel of claim 18 wherein said at least one reactive cationic component has the same reactive functionality as at least one of said silicone containing components.

21. The silicone hydrogel of claim 1 wherein said kinetic half life ratio is at least about 3.

22. The silicone hydrogel of claim 1 further comprising a Dk of at least about 80 barrers.

23. The silicone hydrogel of claim 1 further comprising a Dk of at least about 85 barrers.

24. The silicone hydrogel of claim 1 further comprising a % haze of less than about 70%.

25. The silicone hydrogel of claim 1 further comprising a % haze of less than about 50%.

26. The silicone hydrogel of claim 1 further comprising a water content of at least about 55%.

27. The silicone hydrogel of claim 1 further comprising a water content of at least about 60%.

28. The silicone hydrogel of claim 1 further comprising a modulus of less than about 150 psi.

29. The silicone hydrogel of claim 1 further comprising a modulus of about 100 psi or less.

30. The silicone hydrogel of claim 1 wherein said reaction mixture further comprises at least one UV absorbing compound.

31. The silicone hydrogel of claim 30 wherein said at least one UV absorbing compound is reactive.

32. The silicone hydrogel of claim 30 wherein said at least one UV absorbing compound is selected from benzotriazoles.

33. The silicone hydrogel of claim 30 wherein said at least one UV absorbing compound is selected from the group consisting of reactive 2-(2'-hydroxyphenyl)benzotriazoles, 2-hydroxybenzophenones, 2-hydroxyphenyltriazines, oxanilides, cyanoacrylates, salicylates and 4-hydroxybenzoates.

34. The silicone hydrogel of claim 30 wherein said at least one UV absorbing compound is selected from the group consisting of 2-(2'-hydroxy-5-methacrylyloxyethylphenyl)-2H-benzotriazole, 5-vinyl and 5-isopropenyl derivatives of 2-(2,4-dihydroxyphenyl)-2H-benzotriazole and 4-acrylates or 4-methacrylates of 2-(2,4-dihydroxyphenyl)-2H-benzotriazole or 2-(2,4-dihydroxyphenyl)-1,3-2H-dibenzotriazole, and mixtures thereof.

35. The silicone hydrogel of claim 30 comprising between about 0.5 and about 4 wt. %, of at least one UV absorber.

36. The silicone hydrogel of claim 30 comprising between about 1 wt % and about 2 wt % UV absorber.

37. The silicone hydrogel of claim 1 wherein said reaction mixture is substantially free of diluent.

38. The silicone hydrogel of claim 1 wherein said reaction mixture is substantially free of 3-methacryloxypropyltris(trimethylsiloxy)silane.

39. The silicone hydrogel of claim 1 wherein said slow-reacting hydrophilic monomer comprises a reactive group selected from the group consisting of (meth)acrylamides, vinyls, allyls and combinations thereof and said silicone-containing component comprises a reactive group selected from the group consisting of (meth)acrylates, styryls, amides and mixtures thereof.

40. The silicone hydrogel of claim 1 wherein said slow-reacting hydrophilic monomer comprises a reactive group selected from the group consisting of vinyls, allyls and combinations thereof and said silicone-containing component comprises a reactive group selected from the group consisting of (meth)acrylates, styryls, amides and mixtures thereof.

41. The silicone hydrogel of claim 1 wherein said slow-reacting hydrophilic monomer is present in an amount between about 39 and about 70 wt %.

42. The silicone hydrogel of claim 1 wherein said slow-reacting hydrophilic monomer is present in an amount between about 39 and about 60 wt %.

43. The silicone hydrogel of claim 1 wherein said slow-reacting hydrophilic monomer comprises a reactive group selected from the group consisting of N-vinyl amides, O-vinyl carbamates, O-vinyl carbonates, N-vinyl carbamates, O-vinyl ethers, O-2-propenyl, wherein the vinyl or allyl groups may be further substituted with a methyl group.

44. The silicone hydrogel of claim 1 wherein said slow reacting hydrophilic monomer comprises at least one hydrophilic group selected from the group consisting of hydroxyls, amines, ethers, amides, ammonium groups, carboxylic acid, carbamates and combinations thereof.

45. The silicone hydrogel of claim 1 wherein said slow reacting hydrophilic monomer comprises at least one hydrophilic group selected from the group consisting of hydroxyls, ethers, amides, carboxylic acid combinations thereof.

46. The silicone hydrogel of claim 1 wherein said slow reacting hydrophilic monomer is selected from N-vinylamide monomer of Formula I, a vinyl pyrrolidone of Formula II-IV, n-vinyl piperidone of Formula V:

Formula I

Formula II

Formula III

Formula IV

Formula V wherein R is H or methyl;

$R_1$, $R_2$, $R_3$, $R_6$, $R_7$, $R_{10}$, and $R_{11}$ are independently selected from H, $CH_3$, $CH_2CH_3$, $CH_2CH_2CH_3$, $C(CH_3)_2$;

$R_4$ and $R_8$ are independently selected from $CH_2$, $CHCH_3$ and $C(CH_3)$;

$R_5$ is selected from H, methyl, ethyl; and $R_9$ is selected from $CH=CH_2$, $CCH_3=CH_2$, and $CH=CHCH_3$.

47. The silicone hydrogel of claim 46 wherein the slow-reacting hydrophilic monomer is selected from the vinyl pyrrolidone of Formula II or IV or the N-vinyl amide monomer of Formula I, and the total number of carbon atoms in $R_1$ and $R_2$ is 4 or less.

48. The silicone hydrogel of claim 46 wherein the slow-reacting hydrophilic monomer is selected from a vinyl pyrrolidone of Formula III or IV and $R_6$ is methyl, $R_7$ is hydrogen, $R_9$ is $CH=CH_2$, $R_{10}$ and $R_{11}$ are H.

49. The silicone hydrogel of claim 1 wherein the slow-reacting hydrophilic monomer is selected from the slow-reacting hydrophilic monomer is selected from ethylene glycol vinyl ether (EGVE), di(ethylene glycol) vinyl ether (DEGVE), N-vinyl pyrrolidone (NVP), 1-methyl-3-methylene-2-pyrrolidone, 1-methyl-5-methylene-2-pyrrolidone, 5-methyl-3-methylene-2-pyrrolidone; 1-ethyl-5-methylene-2-pyrrolidone, N-methyl-3-methylene-2-pyrrolidone, 5-ethyl-3-methylene-2-pyrrolidone, 1-n-propyl-3-methylene-2-pyrrolidone, 1-n-propyl-5-methylene-2-pyrrolidone, 1-isopropyl-3-methylene-2-pyrrolidone, 1-isopropyl-5-methylene-2-pyrrolidone, N-vinyl-N-methyl acetamide (VMA), N-vinyl-N-ethyl acetamide, N-vinyl-N-ethyl formamide, N-vinyl formamide, N-vinyl acetamide, N-vinyl isopropylamide, allyl alcohol, N-vinyl caprolactam, N-2-hydroxyethyl vinyl carbamate, N-carboxy-β-alanine N-vinyl ester; N-carboxyvinyl-β-alanine (VINAL), N-carboxyvinyl-α-alanine and mixtures thereof.

50. The silicone hydrogel of claim 1 wherein the slow-reacting hydrophilic monomer is selected from NVP, VMA and 1-methyl-5-methylene-2-pyrrolidone.

51. The silicone hydrogel of claim 1 wherein the slow-reacting hydrophilic monomer comprises NVP.

52. The silicone hydrogel of claim 1 wherein said silicone-containing component comprises at least one hydroxyl group.

53. The silicone hydrogel of claim 1 further comprising at least one hydroxyalkyl monomer.

54. The silicone hydrogel of claim 53 wherein said hydroxyalkyl monomer is selected from hydroxyalkyl (meth)acrylate or (meth)acrylamide monomer of Formula VII or a styryl compound of Formula VIII

FORMULA VII

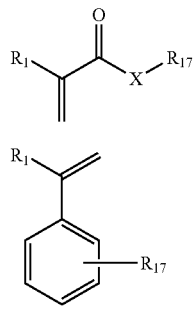

FORMULA VIII wherein $R_1$ is H or methyl,
X is O or $NR_{16}$, $R_{16}$ is a H, $C_1$ to $C_4$ alkyl, which may be further substituted with at least one OH, and
$R_{17}$ is selected from $C_2$-$C_4$ mono or dihydroxy substituted alkyl, and poly(ethylene glycol) having 1-10 repeating units.

55. The silicone hydrogel of claim 53 wherein $R_1$ is H or methyl, X is oxygen and R is selected from $C_2$-$C_4$ mono or dihydroxy substituted alkyl, and poly(ethylene glycol) having 1-10 repeating units.

56. The silicone hydrogel of claim 53 wherein $R_1$ methyl, X is oxygen and R is selected from $C_2$-$C_4$ mono or dihydroxy substituted alkyl, and poly(ethylene glycol) having 2-20 repeating units.

57. The silicone hydrogel of claim 53 wherein said hydroxyalkyl monomer is selected from 2-hydroxyethyl methacrylate, 2-hydroxyethyl acrylate, 3-hydroxypropyl (meth)acrylate, 2-hydroxypropyl (meth)acrylate, 1-hydroxypropyl-2-(meth)acrylate, 2-hydroxy-2-methyl-propyl (meth)acrylate, 3-hydroxy-2,2-dimethyl-propyl (meth)acrylate, 4-hydroxybutyl (meth)acrylate, glycerol (meth)acrylate, 2-hydroxyethyl (meth)acrylamide, polyethyleneglycol monomethacrylate, bis-(2-hydroxyethyl) (meth)acrylamide, 2,3-dihydroxypropyl (meth)acrylamide, and mixtures thereof.

58. The silicone hydrogel of claim 53 wherein said hydroxyalkyl monomer is selected from the group consisting of 2-hydroxyethyl methacrylate, glycerol methacrylate, 2-hydroxypropyl methacrylate, hydroxybutyl methacrylate, 3-hydroxy-2,2-dimethyl-propyl methacrylate, and mixtures thereof.

59. The silicone hydrogel of claim 53 wherein said hydroxyalkyl monomer comprises 2-hydroxyethyl methacrylate, 3-hydroxy-2,2-dimethyl-propyl methacrylate, glycerol methacrylate and mixtures comprising them.

60. The silicone hydrogel of claim 1 wherein the at least one silicone-containing monomer is monofunctional and comprises (a) a reactive group selected from (meth)acrylates, styryls, amides and mixtures thereof and (b) a polydialkyl siloxane chain and may optionally contain fluorine.

61. The silicone hydrogel of claim 1 wherein said silicone-containing component is selected from mono (meth)acryloxyalkyl polydialkylsiloxane monomer of Formula IX or the styryl polydialkylsiloxane monomer of Formula X:

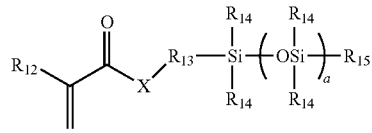

Formula IX

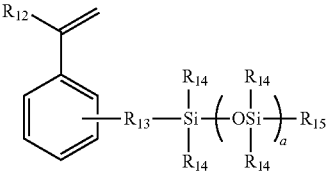

Formula X wherein $R_{12}$ is H or methyl;
X is O or $NR_{16}$;
each $R_{14}$ is independently a $C_1$ to $C_4$ alkyl which may be fluorine substituted, or phenyl;
$R_{15}$ is a $C_1$ to $C_4$ alkyl;
$R_{13}$ is a divalent alkyl group, which may further be functionalized with a group selected from the group consisting of ether groups, hydroxyl groups, carbamate groups and combinations thereof;
a is 3 to 50;
$R_{16}$ is selected from H, $C_1$-$C_4$, which may be further substituted with one or more hydroxyl groups.

62. The silicone hydrogel of claim 61 wherein each $R_{14}$ is independently selected from ethyl and methyl groups.

63. The silicone hydrogel of claim 61 wherein all $R_{14}$ are methyl.

64. The silicone hydrogel of claim 61 wherein $R_{12}$ and each $R_{14}$ are methyl.

65. The silicone hydrogel of claim 61 wherein at least one $R_{14}$ is 3,3,3-trifluoropropyl.

66. The silicone hydrogel of claim 61 wherein $R_{13}$ is selected from $C_1$-$C_6$ alkylene groups which may be substituted with ether, hydroxyl and combinations thereof.

67. The silicone hydrogel of claim 61 wherein $R_{13}$ is selected from C1 or $C_3$-$C_6$ alkylene groups which may be substituted with ether, hydroxyl and combinations thereof.

68. The silicone hydrogel of claim 61 wherein a is 5 to 15.

69. The silicone hydrogel of claim 61 wherein $R_{16}$ is H or methyl.

70. The silicone hydrogel of claim 61 wherein said monomethacryloxyalkylpolydimethylsiloxane methacrylate is selected from the group consisting of monomethacryloxypropyl terminated mono-n-butyl terminated polydimethylsiloxane, monomethacryloxypropyl terminated mono-n-methyl terminated polydimethylsiloxane, monomethacryloxypropyl terminated mono-n-butyl terminated polydiethylsiloxane, monomethacryloxypropyl terminated mono-n-methyl terminated polydiethylsiloxane, N-(2,3-dihydroxypropane)-N'-(propyl tetra(dimethylsiloxy) dimethylbutylsilane)acrylamide, α-(2-hydroxy-1-methacryloxypropyloxypropyl)-ω-butyl-octamethylpentasiloxane, and mixtures thereof.

71. The silicone hydrogel of claim 61 wherein said monomethacryloxyalkylpolydimethylsiloxane methacrylate is selected from the group consisting of monomethacryloxypropyl terminated mono-n-butyl terminated polydimethylsiloxane, monomethacryloxypropyl terminated mono-n-methyl terminated polydimethylsiloxane, N-(2,3-dihydroxypropane)-N'-(propyl tetra(dimethylsiloxy) dimethylbutylsilane)acrylamide, and mixtures thereof.

72. The silicone hydrogel of claim 1 further comprising at least one crosslinking monomer.

73. The silicone hydrogel of claim 1 wherein further comprising at least one photoinitiator.

74. The silicone hydrogel of claim 1 further comprising an advancing contact angle of less than about 80°.

75. The silicone hydrogel of claim 1 further comprising an advancing contact angle of less than about 70°.

76. The silicone hydrogel of claim 1 further comprising from about 5 to about 20 wt % of at least one polar diluent, based upon all components in the reaction mixture.

77. The silicone hydrogel of claim 1 wherein said reaction mixture further comprises at least one slow reacting crosslinker and at least one fast reacting crosslinker.

78. The silicone hydrogel of claim 77 wherein said slow reacting crosslinkers have only vinyl reactive functionality and said fast reacting crosslinkers have (meth)acrylate reactive functionality only.

79. The silicone hydrogel of claim 77 wherein said slow reacting crosslinker comprises triallylcyanurate and said fast reacting crosslinker is selected from the group consisting of ethylene glycol dimethacrylate, tetraethyleneglycol dimethacrylate and mixtures thereof.

80. The silicone hydrogel of claim 1 wherein said reaction mixture further comprises less than about 5% of an intermediate reacting hydrophilic components which have a kinetic half life between 20% and 70% faster than the slowest reacting silicone component.

81. The silicone hydrogel of claim 77 wherein said at least one slow reacting crosslinker and at least one fast reacting crosslinker are each present in said reaction mixture in amounts between about 0.05 to about 0.3 wt %.

82. The silicone hydrogel of claim 77 wherein said at least one slow reacting crosslinker and at least one fast reacting crosslinker are each present in said reaction mixture in amounts between about 0.1 to about 0.2 wt %.

83. The silicone hydrogel of claim 77 wherein all crosslinkers are present in an amount less than about 0.5 wt %.

84. The silicone hydrogel of claim 1 wherein said at least one pharmaceutical pharmaceutical or neutraceutical component is cationic.

85. The silicone hydrogel of claim 1 wherein said at least one pharmaceutical pharmaceutical or neutraceutical component is selected from the group consisting of atropine, pirenzepine, doxycycline, brimonidine, brinzolamide, dorzolamide, betaxolol, apraclonidine, ccr2 antagonist, olopatadine, alcaftadine, betaxolol, bupivacaine, carbachol, carteolol, chlortetracycline, cyclopentolate, dibutoline, dipivefrin, ephedrine, erythromycin, gentamycin, gramicidin, homatropine ketotifen, levobunolol, levocabastine, lidocaine, lignocaine, lomefloxacin, mepivacaine, naphazoline, neomycin, ofloxacin, oxybuprocaine, pheniramine, physostigmine, pilocarpine, polymyxin B, proparacaine, pyrilamine, tetracaine, tetracycline, tetrahydozoline, timolol, tropicamide, vidarabine, pharmaceutically acceptable salts thereof and combinations thereof and the like.

86. The silicone hydrogel of claim 1 wherein said at least one pharmaceutical pharmaceutical or neutraceutical component is selected from the group consisting of atropine, pirenzepine, doxycycline, brimonidine, brinzolamide, dorzolamide, betaxolol, apraclonidine, ccr2 antagonist, olopatadine, alcaftadine, betaxolol, bupivacaine, carbachol, carteolol, chlortetracycline, cyclopentolate, dibutoline, dipivefrin, erythromycin, gentamycin, gramicidin, homatropine ketotifen, levobunolol, levocabastine, lidocaine, lignocaine, lomefloxacin, mepivacaine, naphazoline, ofloxacin, pheniramine, physostigmine, pilocarpine, polymyxin B, proparacaine, pyrilamine, tetracaine, tetrahydozoline, timolol, tropicamide pharmaceutically acceptable salts thereof and combinations thereof and the like.

87. The silicone hydrogel of claim 1 wherein said at least one pharmaceutical pharmaceutical or nutraceutical component is selected from the group consisting of atropine, ketotifen, olopatadine, alcaftadine, levocabastine, pirenzepine, doxycycline, brimonidine, brinzolamide, dorzolamide, betaxolol, apraclonidine, ccr2 antagonist, olopatadine pharmaceutically acceptable salts thereof and combinations thereof and the like.

88. The silicone hydrogel of claim 1, 85, 86 or 87, wherein said at least one pharmaceutical or nutraceutical component in a symptom mitigating effective amount.

89. The silicone hydrogel of claim 88 wherein said symptom mitigating effective amount is between about 5 μg and about less than 200 μg.

90. The silicone hydrogel of claim 88 wherein said symptom mitigating effective amount is between about 9 μg and about 100 μg.

91. The silicone hydrogel of claim 88 wherein said symptom mitigating effective amount alleviates symptoms for between about 5 minutes, and about 12 hours from insertion of said contact lens on a human's eye.

92. The silicone hydrogel of claim 1 wherein said contact lens comprises a modulus which increases less than about 30% after three autoclave cycles.

* * * * *

UNITED STATES PATENT AND TRADEMARK OFFICE
CERTIFICATE OF CORRECTION

PATENT NO. : 9,125,808 B2
APPLICATION NO. : 13/829688
DATED : September 8, 2015
INVENTOR(S) : Alli et al.

Page 1 of 1

It is certified that error appears in the above-identified patent and that said Letters Patent is hereby corrected as shown below:

Claim 49, Column 48, Lines 59-61 from:
"...the slow-reacting hydrophilic monomer is selected from the slow-readting hydrophilic monomer is selected from ethylene gly-"
To read:
-- ...the slow-reacting hydrophilic monomer is selected from ethylene gly- --

Claim 84, Column 52, Line 2 from:
"one pharmaceutical pharmaceutical or neutraceutical compo-"
To read:
-- one pharmaceutical or neutraceutical compo- --

Claim 85, Column 52, Line 5 from:
"one pharmaceutical pharmaceutical or neutraceutical compo-"
To read:
-- one pharmaceutical or neutraceutical compo- --

Claim 86, Column 52, Line 19 from:
"one pharmaceutical pharmaceutical or neutraceutical compo-"
To read:
-- one pharmaceutical or neutraceutical compo- --

Claim 87, Column 52, Line 33 from:
"one pharmaceutical pharmaceutical or neutraceutical compo-"
To read:
-- one pharmaceutical or neutraceutical compo- --

Signed and Sealed this
Eighth Day of March, 2016

Michelle K. Lee
*Director of the United States Patent and Trademark Office*